US 9,377,689 B2

United States Patent
Takemura et al.

(10) Patent No.: US 9,377,689 B2
(45) Date of Patent: Jun. 28, 2016

(54) SILICONE STRUCTURE-BEARING POLYMER, NEGATIVE RESIST COMPOSITION, PHOTO-CURABLE DRY FILM, PATTERNING PROCESS, AND ELECTRIC/ELECTRONIC PART-PROTECTING FILM

(71) Applicant: SHIN-ETSU CHEMICAL CO., LTD., Tokyo (JP)

(72) Inventors: Katsuya Takemura, Joetsu (JP); Hiroyuki Urano, Joetsu (JP); Masashi Iio, Joetsu (JP); Takayuki Fujiwara, Joetsu (JP); Koji Hasegawa, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 14/807,072

(22) Filed: Jul. 23, 2015

(65) Prior Publication Data
US 2016/0033865 A1 Feb. 4, 2016

(30) Foreign Application Priority Data

Jul. 29, 2014 (JP) .................. 2014-153677

(51) Int. Cl.
| | | |
|---|---|---|
| *G03F 7/075* | (2006.01) | |
| *C08G 77/52* | (2006.01) | |
| *G03F 7/40* | (2006.01) | |
| *G03F 7/38* | (2006.01) | |
| *C07C 39/21* | (2006.01) | |
| *C09D 183/14* | (2006.01) | |
| *C08L 83/14* | (2006.01) | |
| *H01L 21/312* | (2006.01) | |
| *C08G 77/12* | (2006.01) | |
| *G03F 7/16* | (2006.01) | |
| *G03F 7/20* | (2006.01) | |
| *G03F 7/32* | (2006.01) | |
| *G03F 7/038* | (2006.01) | |
| *G03F 7/09* | (2006.01) | |
| *G03F 7/11* | (2006.01) | |

(52) U.S. Cl.
CPC .............. *G03F 7/0757* (2013.01); *C07C 39/21* (2013.01); *C08G 77/12* (2013.01); *C08L 83/14* (2013.01); *C09D 183/14* (2013.01); *G03F 7/038* (2013.01); *G03F 7/0382* (2013.01); *G03F 7/09* (2013.01); *G03F 7/11* (2013.01); *G03F 7/168* (2013.01); *G03F 7/2002* (2013.01); *G03F 7/2037* (2013.01); *G03F 7/32* (2013.01); *G03F 7/38* (2013.01); *G03F 7/40* (2013.01); *H01L 21/312* (2013.01); *C08G 77/52* (2013.01)

(58) Field of Classification Search
None
See application file for complete search history.

(56) References Cited

U.S. PATENT DOCUMENTS

| | | | |
|---|---|---|---|
| 3,159,601 | A | 12/1964 | Ashby |
| 3,159,662 | A | 12/1964 | Ashby |
| 3,220,972 | A | 11/1965 | Lamoreaux |
| 3,775,452 | A | 11/1973 | Karstedt |
| 7,700,403 | B2 | 4/2010 | Arai et al. |
| 7,785,766 | B2 | 8/2010 | Kato et al. |
| 2002/0055550 | A1 | 5/2002 | Kato et al. |
| 2008/0182087 | A1 | 7/2008 | Kato et al. |
| 2011/0076465 | A1 | 3/2011 | Takeda et al. |
| 2013/0149493 | A1 | 6/2013 | Takemura et al. |
| 2013/0149645 | A1 | 6/2013 | Takemura et al. |
| 2015/0056545 | A1* | 2/2015 | Urano ............... C08G 77/38 430/18 |

FOREIGN PATENT DOCUMENTS

| | | |
|---|---|---|
| EP | 1186624 A1 | 3/2002 |
| EP | 1953183 A2 | 8/2008 |
| EP | 2305754 A1 | 4/2011 |
| EP | 2602660 A1 | 6/2013 |
| EP | 2602661 A1 | 6/2013 |
| JP | 2008-184571 A | 8/2008 |
| JP | 2009-200315 A | 9/2009 |

OTHER PUBLICATIONS

European Search Report dated Oct. 7, 2015, issued in counterpart Application No. 15178644.9-1301 (4 pages).

* cited by examiner

Primary Examiner — Cynthia Hamilton
(74) Attorney, Agent, or Firm — Westerman, Hattori, Daniels & Adrian, LLP

(57) ABSTRACT

A silicone structure-bearing polymer comprising recurring units derived from a bis(4-hydroxy-3-allylphenyl) derivative and having a Mw of 3,000-500,000 is provided. A chemically amplified negative resist composition comprising the polymer overcomes the stripping problem that a coating is stripped from metal wirings of Cu or Al, electrodes, and SiN substrates.

15 Claims, 1 Drawing Sheet

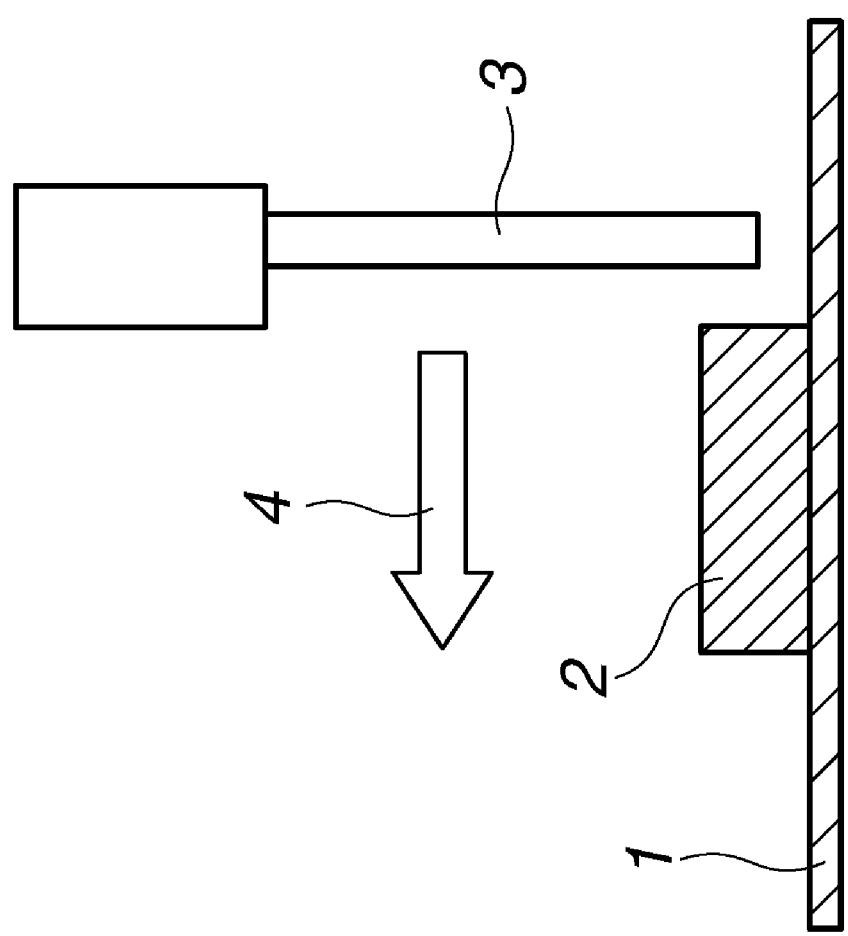

SILICONE STRUCTURE-BEARING POLYMER, NEGATIVE RESIST COMPOSITION, PHOTO-CURABLE DRY FILM, PATTERNING PROCESS, AND ELECTRIC/ELECTRONIC PART-PROTECTING FILM

CROSS-REFERENCE TO RELATED APPLICATION

This non-provisional application claims priority under 35 U.S.C. §119(a) on Patent Application No. 2014-153677 filed in Japan on Jul. 29, 2014, the entire contents of which are hereby incorporated by reference.

TECHNICAL FIELD

This invention relates to a silicone structure-bearing polymer; a chemically amplified negative resist composition comprising the silicone structure-bearing polymer which can be patterned by exposure to ultraviolet radiation in near-UV and deep-UV regions having a wavelength below 500 nm such as i and g-line; a photo-curable dry film using the resist composition; a method of preparing the photo-curable dry film; a pattern forming process comprising applying the resist composition or dry film to form a resist film or photo-curable resin layer on a substrate and patterning; and a film for the protection of electric/electronic parts (e.g., wirings, circuits and boards) obtained by curing the resist film or photo-curable resin layer. The invention further relates to a bis(4-hydroxy-3-allylphenyl) derivative useful as a starting reactant to the silicone structure-bearing polymer.

Patterned films of a negative resist composition are used to cover wirings, circuits, boards or the like as protective film. However, when patterns formed of negative resist composition are applied to wirings, circuit-forming metal (typically Cu) layers, metal (typically Al) electrodes on substrates, or SiN substrates (serving as dielectric substrates bearing wirings or circuits to be covered), a stripping problem often arises that the patterns are stripped from the underlying substrate owing to poor adhesion. Surprisingly, a pattern formed of a chemically amplified negative resist composition according to the invention or a dry film comprising the composition is significantly improved in adhesion to substrate.

Owing to its advantages including heat resistance, chemical resistance, insulation and flexibility, the protective film formed of the resist composition of the invention finds use as dielectric film for semiconductor devices including redistribution, dielectric film for multilayer printed boards, solder mask, cover lay film, dielectric film for filling in through-silicon vias (TSV), and lamination of substrates.

BACKGROUND ART

As most electronic equipment including personal computers, digital cameras and mobile phones become of smaller size and better performance, there is an increasing demand for semiconductor devices of small size, thin profile and high density. There is a desire to have a photosensitive dielectric material which can accommodate an increase of substrate area for productivity improvement and which can accommodate structures having fine asperities with a high aspect ratio on substrates in the high-density packaging technology as typified by chip size packages or chip scale packages (CSP) or 3D layer stacks.

With respect to the photosensitive dielectric material mentioned above, JP-A 2008-184571 discloses a photo-curable resin composition which can be coated to form films having a widely varying thickness by the spin coating technique commonly used in the semiconductor device fabrication, processed into fine size patterns using radiation of a wide wavelength range, and post-cured at low temperatures into electric/electronic part-protecting films having flexibility, heat resistance, electric properties, adhesion, reliability and chemical resistance. Advantageously, the spin coating technique is capable of simply forming a film on a substrate.

This photo-curable resin composition for forming electric/electronic part-protecting films is used to form a film having a thickness of 1 to 100 μm on a substrate. As the film thickness increases beyond 30 μm, it becomes difficult to apply the photo-curable resin composition onto the substrate by spin coating because the composition must have a very high viscosity. The film formation on substrate by spin coating encounters a certain limit in the practical application.

Also, when the photo-curable resin composition is applied onto a substrate having a rugged surface by spin coating, it is difficult to form a uniform layer on the substrate. The photo-curable resin layer tends to leave voids near steps on the substrate. Further improvements in planarity and step coverage are desired. Another coating technique replacing the spin coat technique is spray coating as disclosed in JP-A 2009-200315. Owing to the principle of spraying, defects are often formed including height difference arising from asperities on the substrate, film rupture at pattern edges and pinholes at recess bottom. The problems of planarity and step coverage still remain unsolved.

Recently, in the high-density package technology as typified by chip scale packages (CSP) or 3D stacked packages, a focus is put on the technique of redistribution from chips by forming a fine, high aspect ratio pattern on a substrate and depositing a metal such as copper on the pattern. To meet a demand for chips of higher density and higher integration, it is strongly desired to reduce the width of pattern lines and the size of contact holes for interconnection between substrates in the redistribution technology. The lithography is generally used for forming fine size patterns. In particular, the lithography combined with chemically amplified negative resist compositions is best suited for forming fine pattern features. Since the pattern used for redistribution is permanently left between device chips, the pattern material must have a cure ability and also serve as an electric/electronic part-protecting film having flexibility, heat resistance, electric properties, adhesion, reliability and chemical resistance. For this reason, a negative resist composition is believed suitable for forming such patterns.

Accordingly, a chemically amplified negative resist composition is typical of the pattern-forming material which can be processed into a fine redistribution layer and serve as an electric/electronic part-protecting film having flexibility, heat resistance, electric properties, adhesion, reliability and chemical resistance.

On the other hand, a chemically amplified negative resist composition can form a fine pattern as used in the redistribution technology and is useful as electric/electronic part-protecting film. The negative resist composition is thus often used to cover Cu wirings preformed on substrates, Al electrodes on substrates, or dielectric or SiN substrates having wirings or electrodes formed thereon. Sometimes, the negative resist composition must entirely cover the SiN substrate. Since the adhesion between the coating layer of the negative resist composition and the substrate is still insufficient, a stripping problem often arises that the coating layer is stripped from the substrate.

When the chemically amplified negative resist composition useful to form electric/electronic part-protecting film is patterned, an organic solvent is used as the developer. It is necessary that the exposed region of resist film be turned insoluble in the organic solvent developer via crosslinking reaction or the like while the unexposed region be fully dissolved in the organic solvent developer. Most of commonly used negative resist compositions have a low dissolution contrast, that is, a small difference of solubility in organic solvent developer between the exposed and unexposed regions. A resist composition with a low dissolution contrast is not expectable to form a pattern which is satisfactory with respect to the requirement for finer size patterns. Also when a pattern is exposed and transferred through a mask, a resist composition with a low dissolution contrast may fail to form a pattern faithful to the mask on the substrate. Accordingly, the resist composition is desired to have as high a dissolution contrast as possible, that is, an improvement in resolution is desired.

Furthermore, for the chemically amplified negative resist composition capable of forming a fine size pattern used in processing of interconnects, and useful to form electric/electronic part-protecting film, it is important that the unexposed region is fully dissolved in the organic solvent developer. If the solubility of the unexposed region in the organic solvent developer is low, then it is often observed that film residue or scum is left at the bottom of the pattern, or the pattern is degraded by footing at the root of the pattern on the substrate, particularly when the coating of the resist composition on the substrate is thick. Since such scumming or footing can cause breakage or damage to the electric circuit and interconnect during the redistribution step, it is necessary to inhibit scumming or footing.

Accordingly, to meet a demand for chips of higher density and higher integration, it is desired to have a chemically amplified negative resist composition which can form a fine size pattern for redistribution, and is suited as electric/electronic part-protecting film. The resist composition is further desired to dramatically improve its adhesion to substrate, further improve its resolution performance, and eliminate the problem of footing or scumming at the pattern bottom.

CITATION LIST

Patent Document 1: JP-A 2008-184571 (U.S. Pat. No. 7,785,766)
Patent Document 2: JP-A 2009-200315 (U.S. Pat. No. 7,700,403)

SUMMARY OF INVENTION

A first object of the invention is to provide a chemically amplified negative resist composition which is able to form a fine size pattern, overcomes the stripping problem that can be encountered on wirings and electrodes of metal (e.g., Cu or Al), and substrates, typically SiN substrates, and eliminates the problem of footing or scumming on the pattern bottom and the substrate during formation of a fine size pattern; a silicone structure-bearing polymer suitable as base resin in the resist composition; and a phenyl derivative useful in the preparation of the polymer.

A second object is to provide a pattern forming process of forming a fine size pattern simply by spin coating the resist composition onto a substrate.

A third object is to provide a photo-curable dry film comprising the resist composition; and a pattern forming process capable of forming a resist layer having a widely varying thickness even on a substrate having a rugged surface, using the photo-curable dry film.

A fourth object is to provide a protective film for electric and electronic parts such as wirings, circuits and boards, comprising a cured film obtained by post-curing at low temperature the pattern resulting from the pattern forming process.

The inventors have found that (A) a silicone structure-bearing polymer represented by the general formula (1) is obtainable using a bis(4-hydroxy-3-allylphenyl) derivative having an alcoholic hydroxyl group represented by the general formula (6); that a chemically amplified negative resist composition comprising (A) a silicone structure-bearing polymer, (B) a photoacid generator, (C) a crosslinker, and (D) a solvent can form a fine pattern, inhibits footing or scumming between the pattern bottom and the substrate because of the improved solubility of the unexposed region in the organic solvent developer, and substantially overcomes the stripping problem that can be encountered on wirings and electrodes of metal (e.g., Cu or Al), and substrates, typically SiN substrates. The cured film resulting from the pattern forming process using the composition is useful as an electric/electronic part-protecting film.

Embodiments of the invention are defined below.

In a first aspect, the invention provides a silicone structure-bearing polymer comprising recurring units of the general formula (1) and having a weight average molecular weight of 3,000 to 500,000.

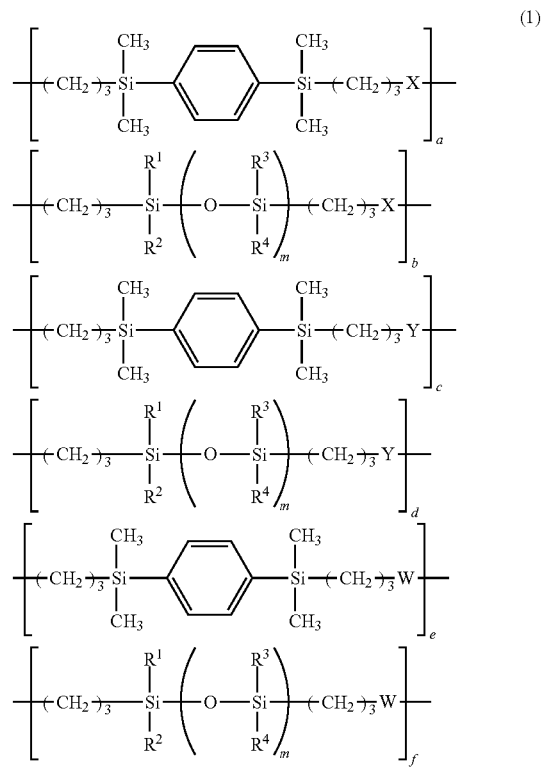

Herein $R^1$ to $R^4$ are each independently a monovalent $C_1$-$C_8$ hydrocarbon group, m is an integer of 1 to 100, a, b, c and d are each independently 0 or a positive number, e and f each are a positive number, and a+b+c+d+e+f=1, X is an organic group having the general formula (2):

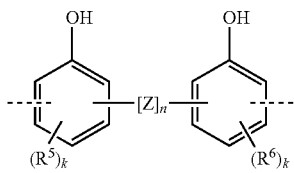
(2)

wherein Z is a divalent organic group selected from the group consisting of

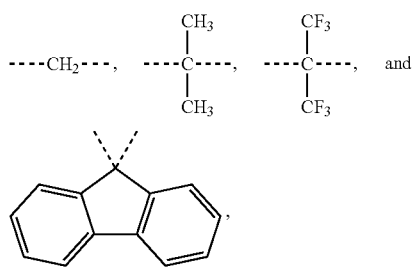

the broken line segment denotes a valence bond, n is 0 or 1, $R^5$ and $R^6$ are each independently a $C_1$-$C_4$ alkyl or alkoxy group, k is 0, 1 or 2, Y is an organic group having the general formula (3):

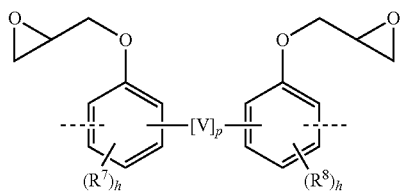
(3)

wherein V is a divalent organic group selected from the group consisting of

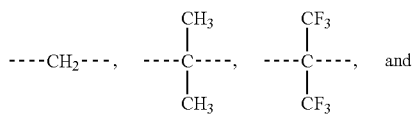

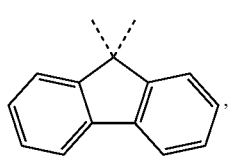

the broken line segment denotes a valence bond, p is 0 or 1, $R^7$ and $R^8$ are each independently a $C_1$-$C_4$ alkyl or alkoxy group, h is 0, 1 or 2, and W is an organic group having the general formula (4):

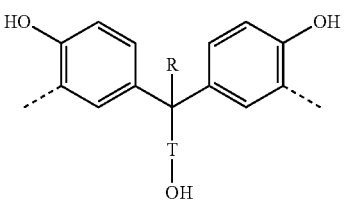
(4)

wherein the broken line segment denotes a valence bond, R is hydrogen or a straight or branched $C_1$-$C_6$ alkyl group, and T is a straight, branched or cyclic $C_1$-$C_{12}$ alkylene group.

In a preferred embodiment, W is an organic group having the general formula (5).

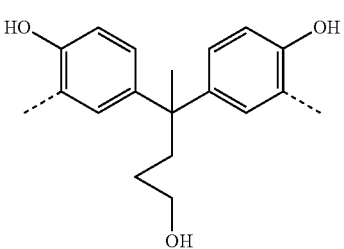
(5)

In formula (1), a to f are preferably in the range: $0.1 \leq a \leq 0.8$, $0.1 \leq b \leq 0.8$, $0 \leq c$, $0 \leq d$, $0 < e \leq 0.8$, and $0 < f \leq 0.8$.

In a second aspect, the invention provides a chemically amplified negative resist composition comprising (A) the silicone structure-bearing polymer having a weight average molecular weight of 3,000 to 500,000, defined above, (B) a photoacid generator which is decomposed to generate an acid upon exposure to radiation of wavelength 190 to 500 nm, (C) at least one crosslinker selected from the group consisting of an amino condensate modified with formaldehyde or formaldehyde-alcohol, a phenol compound having on the average at least two methylol or alkoxymethylol groups in the molecule, a polyhydric phenol compound in which at least one hydrogen atom of hydroxyl group is substituted by a glycidyl group, a polyhydric phenol compound in which at least one hydrogen atom of hydroxyl group is substituted by a group of the formula (C-1), and a compound containing at least two structures each having nitrogen bonded to a glycidyl group, the structure having the formula (C-2) or (C-3),

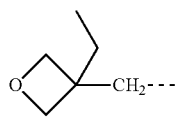
(C-1)

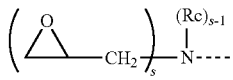
(C-2)

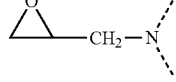
(C-3)

wherein the broken line segment denotes a valence bond, Rc is a straight, branched or cyclic $C_1$-$C_6$ alkyl group, and s is 1 or 2, and (D) a solvent.

In a third aspect, the invention provides a pattern forming process comprising the steps of (1) coating the chemically amplified negative resist composition defined above onto a substrate, and prebaking to form a resist film, (2) exposing the resist film to high-energy radiation of wavelength 190 to 500 nm or electron beam through a photomask, (3) baking and developing in a developer to pattern the resist film.

The process may further comprise (4) post-curing the patterned resist film resulting from development step (3) at a temperature of 100 to 250° C.

In a fourth aspect, the invention provides a photo-curable dry film comprising a photo-curable resin layer having a thickness of 10 to 100 μm sandwiched between a support film and a protective film, the photo-curable resin layer being formed of the chemically amplified negative resist composition defined above.

In a fifth aspect, the invention provides a method for preparing a photo-curable dry film, comprising the steps of (i) continuously coating the chemically amplified negative resist composition defined above onto a support film, (ii) continuously drying the composition to form a photo-curable resin layer on the support film, and (iii) applying a protective film onto the photo-curable resin layer.

In a sixth aspect, the invention provides a pattern forming process comprising the steps of (i) stripping the protective film from the photo-curable dry film defined above and placing the bare photo-curable resin layer in close contact with a substrate, (ii) exposing the photo-curable resin layer to high-energy radiation of wavelength 190 to 500 nm or EB through a photomask and through the support film or with the support film stripped off, (iii) post-exposure bake, and (iv) developing in a developer to pattern the layer.

The process may further include (v) post-curing the patterned layer resulting from development step (iv) at a temperature of 100 to 250° C.

In one embodiment, the substrate is provided with grooves and/or holes having an opening width of 10 to 100 μm and a depth of 10 to 120 μm.

In a seventh aspect, the invention provides a laminate comprising a substrate provided with grooves and/or holes having an opening width of 10 to 100 μm and a depth of 10 to 120 μm, and a layer lying on the substrate, the layer being the photo-curable resin layer of the photo-curable dry film defined above.

In an eighth aspect, the invention provides an electric/electronic part protective film comprising the cured film obtained by the process defined above.

Also contemplated herein is a bis(4-hydroxy-3-allylphenyl) derivative having an alcoholic hydroxyl group, represented by the general formula (6).

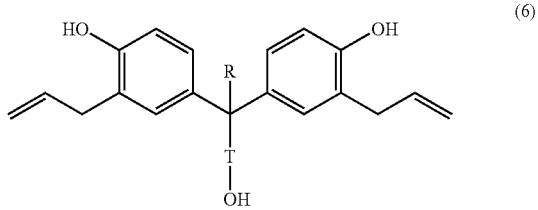

(6)

Herein R is hydrogen or a straight or branched $C_1$-$C_6$ alkyl group and T is a straight, branched or cyclic $C_1$-$C_{12}$ alkylene group.

Typical is 4,4-bis(4-hydroxy-3-allylphenyl)pentanol represented by the formula (7).

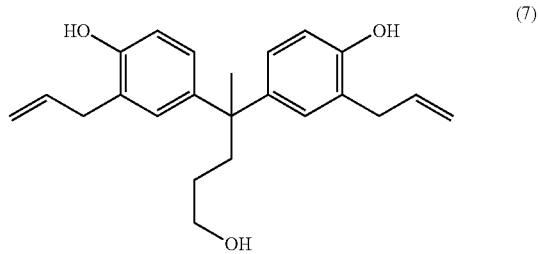 [SMILES: C=CCc1cc(C(C)(CCCO)c2ccc(O)c(CC=C)c2)ccc1O]

(7)

ADVANTAGEOUS EFFECTS OF INVENTION

The chemically amplified negative resist composition substantially overcomes the stripping problem that can be encountered on wirings and electrodes of metal (e.g., Cu or Al), and substrates, typically SiN substrates. The chemically amplified negative resist composition, photo-curable dry film and pattern forming process according to the invention can form a fine pattern using radiation over a wide span of wavelength, can reduce the size of pattern features in the redistribution technology to meet the demand for chips of higher density and higher integration, inhibits footing or scumming on the pattern bottom and the substrate after pattern formation, and are useful to form an electric/electronic part-protecting film.

BRIEF DESCRIPTION OF DRAWINGS

The only FIGURE, FIG. 1 schematically illustrates how to examine adhesion in Examples.

DESCRIPTION OF PREFERRED EMBODIMENTS

The terms "a" and "an" herein do not denote a limitation of quantity, but rather denote the presence of at least one of the referenced item. "Optional" or "optionally" means that the subsequently described event or circumstance may or may not occur, and that the description includes instances where the event occurs and instances where it does not. As used herein, the notation ($C_n$-$C_m$) means a group containing from n to m carbon atoms per group. In the chemical formula, the broken line segment denotes a valence bond.

The abbreviations and acronyms have the following meaning.

Me: methyl
Mw: weight average molecular weight
GPC: gel permeation chromatography
PEB: post-exposure baking
PAG: photoacid generator Silicone Structure-Bearing Polymer One embodiment of the invention is a silicone structure-bearing polymer comprising recurring units represented by the general formula (1) and having a weight average molecular weight (Mw) of 3,000 to 500,000.

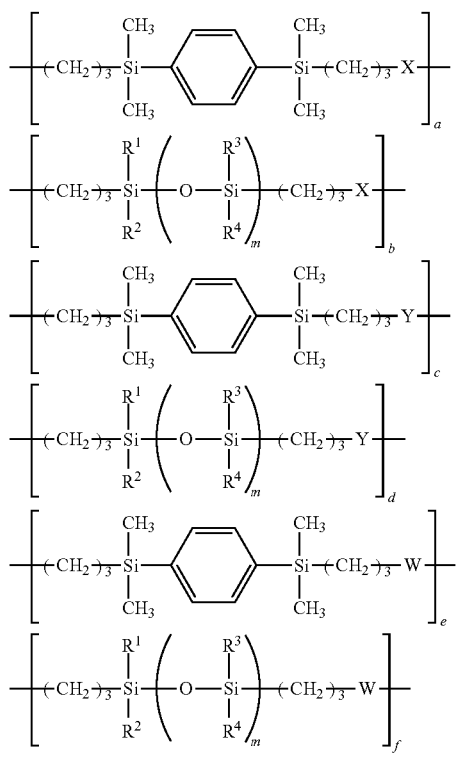

(1)

Herein $R^1$ to $R^4$ are each independently a monovalent $C_1$-$C_8$ hydrocarbon group, m is an integer of 1 to 100, a, b, c and d are each independently 0 or a positive number, e and f each are a positive number, and a+b+c+d+e+f=1, X is an organic group of the general formula (2), Y is an organic group of the general formula (3), and W is an organic group of the general formula (4), shown below.

In formula (1), each of $R^1$ to $R^4$, which may be the same or different, stands for a monovalent hydrocarbon group having 1 to 8 carbon atoms, and preferably 1 to 6 carbon atoms. Examples include straight, branched or cyclic alkyl groups such as methyl, ethyl, propyl, isopropyl, n-butyl, tert-butyl, and cyclohexyl, straight, branched or cyclic alkenyl groups such as vinyl, allyl, propenyl, butenyl, hexenyl, and cyclohexenyl, aryl groups such as phenyl and tolyl, and aralkyl groups such as benzyl and phenylethyl.

From the standpoints of compatibility with a crosslinker and a PAG to be described later and photo-curability, m is an integer of 1 to 100, preferably 1 to 80. From the standpoints of substrate adhesion, electrical properties, and reliability, a, b, c and d each are 0 or a positive number, e and f each are a positive number. Desirably, these subscripts satisfy the range: $0 \le a \le 0.8$, $0.1 \le b \le 0.8$, $0 \le c$, $0 \le d$, $0 < e \le 0.8$, and $0 < f \le 0.8$. Preferably they are in the range: $0 \le a \le 0.8$, more preferably $0.1 \le a \le 0.8$, and even more preferably $0.3 \le a \le 0.7$; $0.1 \le b \le 0.8$, more preferably $0.1 \le b \le 0.5$; $0 \le c \le 0.5$, more preferably $0 \le c \le 0.2$; $0 \le d \le 0.5$, more preferably $0 \le d \le 0.2$; $0 < e \le 0.8$, more preferably $0 < e \le 0.5$; $0 < f \le 0.8$, more preferably $0 < f \le 0.5$, provided that a+b+c+d+e+f=1.

More specifically, these subscripts satisfy the preferred range (i): $0.1 \le a \le 0.8$, $0.1 \le b \le 0.8$, c=d=0, $0 < e \le 0.8$, and $0 < f \le 0.8$; or the preferred range (ii): $0.1 \le a \le 0.7$, $0.1 \le b \le 0.5$, $0 < c \le 0.2$, $0 < d \le 0.2$, $0 < e \le 0.5$, and $0 < f \le 0.5$.

X is an organic group having the general formula (2).

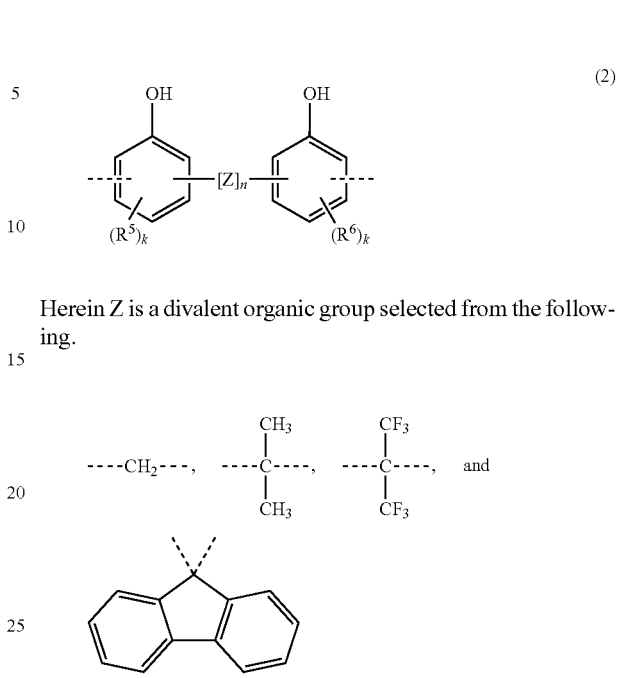

(2)

Herein Z is a divalent organic group selected from the following.

The broken line segment denotes a valence bond, n is 0 or 1, $R^5$ and $R^6$ are each independently a $C_1$-$C_4$ alkyl or alkoxy group, and k is 0, 1 or 2.

Y is an organic group having the general formula (3).

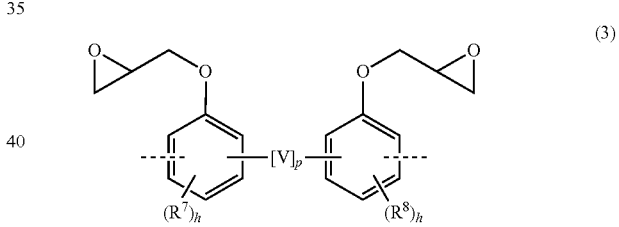

(3)

Herein V is a divalent organic group selected from the following.

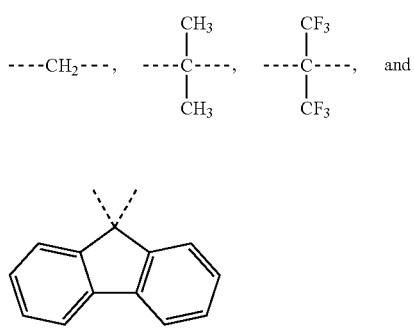

The broken line segment denotes a valence bond, p is 0 or 1, $R^7$ and $R^8$ are each independently a $C_1$-$C_4$ alkyl or alkoxy group, and h is 0, 1 or 2.

W is an organic group having the general formula (4).

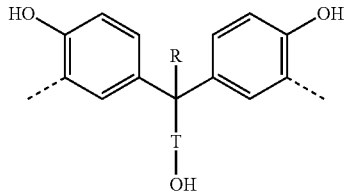

(4)

The broken line segment denotes a valence bond, R is hydrogen or a straight or branched $C_1$-$C_6$ alkyl group, and T is a straight, branched or cyclic $C_1$-$C_{12}$ alkylene group.

Preferably W is an organic group having the general formula (5).

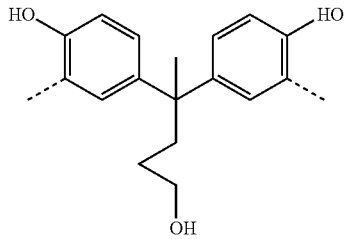

(5)

The silicone structure-bearing polymer should have a weight average molecular weight (Mw) of 3,000 to 500,000 and preferably 5,000 to 300,000, from the standpoints of compatibility and photo-curability of a resist composition comprising the polymer as well as mechanical properties of the cured composition. It is noted that Mw is determined by GPC versus polystyrene standards.

The silicone structure-bearing polymer may be prepared by providing suitable reactants and subjecting them to polymerization reaction, known as "hydrosilylation" reaction, in the presence of a catalyst. The reactants include hydrogensilphenylene, specifically 1,4-bis(dimethylsilyl)benzene, having the formula (8):

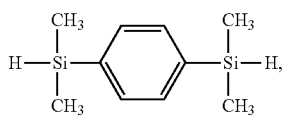

(8)

or a combination of the hydrogensilphenylene (8) with a dihydroorganosiloxane having the formula (9):

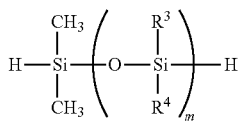

(9)

wherein $R^3$, $R^4$ and m are as defined above, optionally a diallyl-containing epoxy compound having the formula (10):

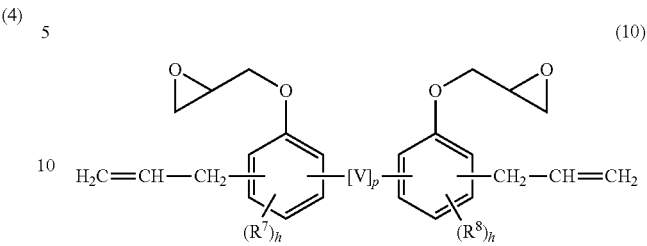

(10)

wherein V, $R^7$, $R^8$, p and h are as defined above, optionally a diallyl-containing phenol compound having the formula (11):

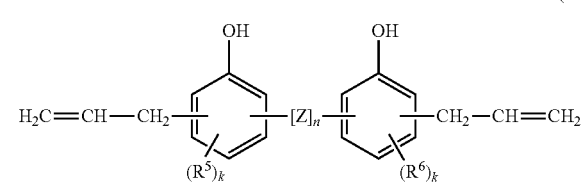

(11)

wherein Z, $R^5$, $R^6$, n and k are as defined above, and a bis(4-hydroxy-3-allylphenyl) derivative having an alcoholic hydroxyl group represented by the formula (6):

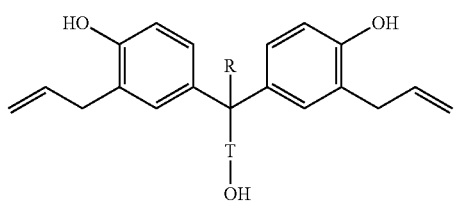

(6)

wherein R and T are as defined above, R is hydrogen or a straight or branched $C_1$-$C_6$ alkyl group, and T is a straight, branched or cyclic $C_1$-$C_{12}$ alkylene group.

The Mw of the silicone structure-bearing polymer may be easily controlled by adjusting a ratio of the total number of allyl groups on the diallyl-containing epoxy compound of formula (10), the diallyl-containing phenol compound of formula (11) and the bis(3-allyl-4-hydroxyphenyl)-containing compound of formula (6), to the total number of hydrosilyl groups on the hydrogensilphenylene of formula (8) and the dihydroorganosiloxane of formula (9) (i.e., total allyl/total hydrosilyl ratio). Alternatively, a polymer having the desired molecular weight may be produced by effecting polymerization of the diallyl-containing epoxy compound, diallyl-containing phenol compound and diallyl-containing, specifically bis(3-allyl-4-hydroxyphenyl)-containing compound with the hydrogensilphenylene and dihydroorganosiloxane while using a monoallyl compound (e.g., o-allylphenol), a monohydrosilane (e.g., triethylhydrosilane) or monohydrosiloxane as a molecular weight modifier.

The catalysts which can be used in the polymerization reaction include platinum group metal elements such as platinum (inclusive of platinum black), rhodium and palladium; platinum chloride, chloroplatinic acid and chloroplatinic acid salts such as $H_2PtCl_4 \cdot xH_2O$, $H_2PtCl_6 \cdot xH_2O$, NaHPtCl$_6$.xH$_2$O, KHPtCl$_6$.xH$_2$O, Na$_2$PtCl$_6$.xH$_2$O, K$_2$PtCl$_4$.xH$_2$O, PtCl$_4$.xH$_2$O, PtCl$_2$, and Na$_2$HPtCl$_4$.xH$_2$O wherein x is specifically an integer of 0 to 6, more specifically 0 or 6; alcohol-modified chloroplatinic acid as described in U.S. Pat. No. 3,220,972; complexes of chloroplatinic acid with olefins as described in U.S. Pat. No. 3,159,601, U.S. Pat. No. 3,159,662 and U.S. Pat. No. 3,775,452; platinum group metals such as platinum black and palladium on supports such as alumina, silica and carbon; rhodium-olefin complexes; chlorotris(triphenylphosphine)rhodium, known as Wilkinson catalyst; and complexes of platinum chloride, chloroplatinic acid or chloroplatinic acid salts with vinyl-containing siloxanes (specifically, vinyl-containing cyclic siloxanes).

The catalyst is used in a catalytic amount, specifically 0.001 to 0.1% by weight of platinum group metal based on the total weight of reactants for polymerization reaction.

If desired, a solvent may be used in the polymerization reaction. Suitable solvents include hydrocarbon solvents such as toluene and xylene. An appropriate amount of the solvent used is 50 to 300 parts, more preferably 100 to 200 parts by weight per 100 parts by weight of the reactants for polymerization reaction in total.

With respect to polymerization conditions, the polymerization temperature is preferably in the range of 40 to 150° C., and more preferably 60 to 120° C. At temperatures within the range, polymerization can be completed within a short time and the catalyst is not deactivated. The polymerization time may vary with the type and amount of a desired polymer. Preferably polymerization is completed within 0.5 to 100 hours, and more preferably 0.5 to 30 hours, in order to prevent moisture entry into the polymerization system. At the end of polymerization, the solvent is distilled off if the solvent is used. In this way, a silicone structure-bearing polymer having formula (1) is obtained.

As the Mw of a silicone structure-bearing polymer lowers, its viscosity also lowers. As a result, a resin layer formed of a chemically amplified negative resist composition comprising that silicone structure-bearing polymer also lowers its viscosity. If a proportion of linear polysiloxane-containing molecular units (corresponding to units (b), (d) and (f) in formula (1)) in the molecule of a silicone structure-bearing polymer increases, a proportion of aromatic compound-containing molecular units, typically silphenylene-containing molecular units (corresponding to units (a), (c) and (e) in formula (1)) relatively decreases. Then the silicone structure-bearing polymer lowers its viscosity. As a result, a resin layer formed of a chemically amplified negative resist composition comprising that silicone structure-bearing polymer also lowers its viscosity. If the linear polysiloxane in the molecule of a silicone structure-bearing polymer increases its molecular chain length, that is, if the value of m in formula (1) increases, the silicone structure-bearing polymer lowers its viscosity. As a result, a resin layer formed of a chemically amplified negative resist composition comprising that silicone structure-bearing polymer may also lower its viscosity.

For the synthesis of the bis(3-allyl-4-hydroxyphenyl) derivative having an alcoholic hydroxyl group represented by formula (6), suitable methods are described below.

In one appropriate synthesis method, the compound of formula (6) may be obtained by starting with a compound having ketone and an alcoholic hydroxyl group, represented by the formula (12-1).

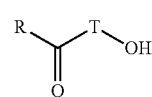
(12-1)

Herein R and T are as defined above.

First, the compound (12-1) having ketone and an alcoholic hydroxyl group may be condensed with about 2 equivalents of phenol under acidic conditions to form a bisphenol derivative having an alcoholic hydroxyl group, represented by the formula (12-2).

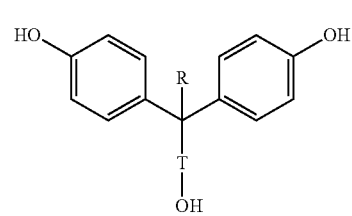
(12-2)

Next, the bisphenol derivative (12-2) having an alcoholic hydroxyl group is reacted with 2 equivalents of allyl halide in an aprotic polar solvent under basic conditions (e.g., potassium carbonate), to substitute allyl for the hydrogen atom of a phenolic hydroxyl group, yielding a compound represented by the formula (12-3).

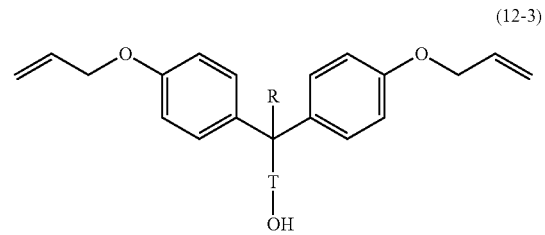
(12-3)

The compound (12-3) having a phenolic hydroxyl group whose hydrogen is substituted by allyl is dissolved in a high-boiling solvent such as dimethylaniline and heated at a high temperature of about 180° C. to incur Claisen rearrangement reaction, yielding the target compound in which allyl is rearranged to the 3-position of phenol, that is, bis(4-hydroxy-3-allylphenyl) derivative having an alcoholic hydroxyl group, represented by formula (6).

In another appropriate synthesis method, the compound of formula (6) may be obtained by starting with a compound having ketone and carboxylic acid, represented by the formula (12-4).

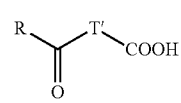
(12-4)

Herein R is as defined above and T' is an alkylene group containing less carbon atoms than T by one.

The compound (12-4) having ketone and carboxylic acid may be condensed with 2 equivalents of phenol under acidic conditions as above to form a bisphenol derivative having carboxylic acid, represented by the formula (12-5).

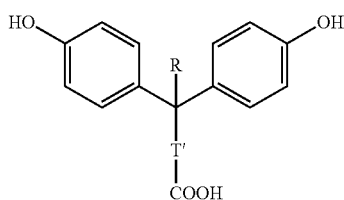

(12-5)

Next, the compound (12-5) is reacted with 3 equivalents of allyl halide under the same conditions as above to form the allyl ether, yielding a compound represented by the formula (12-6). At this point, 2 equivalents of allyl halide serve to substitute allyl for the hydrogen atom of a hydroxyl group of phenol while the remaining 1 equivalent of allyl halide serves to substitute allyl for the hydrogen atom of a carboxyl group to form allyl carboxylate. This results in the compound (12-6).

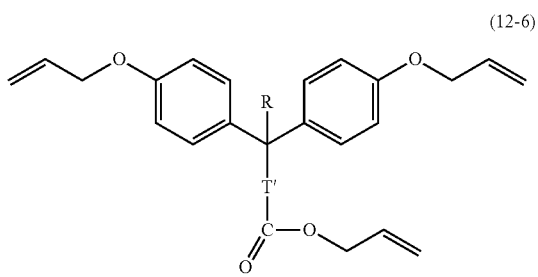

(12-6)

The compound (12-6) is dissolved in an aprotic solvent such as tetrahydrofuran or toluene, to which a solution of at least 1 equivalent, preferably 1 to 1.5 equivalents of sodium bis(2-methoxyethoxy)aluminumhydride (Red-Al®) or reducing agent is added. The resulting solution is stirred at a temperature of 0 to 30° C., preferably 0 to 15° C. to induce reductive reaction on the carboxylic acid site, yielding a compound of the formula (12-7) similar to formula (12-3).

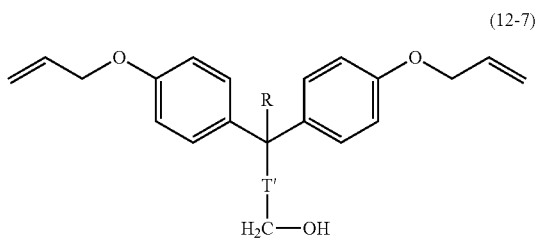

(12-7)

Subsequently, the compound (12-7) is subjected to Claisen rearrangement reaction as above, yielding the target compound in which allyl is rearranged to the 3-position of phenol, that is, a derivative of the following formula (12-8) similar to the bis(4-hydroxy-3-allylphenyl) derivative having an alcoholic hydroxyl group, represented by formula (6).

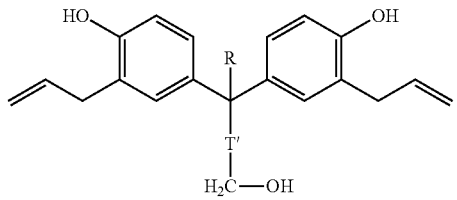

(12-8)

In the method for preparing the bis(4-hydroxy-3-allylphenyl) derivative having an alcoholic hydroxyl group, represented by formula (6) through the above-described series of steps, diphenolic acid of the following formula (12-9) is preferably used as the bisphenol derivative (12-5) having carboxylic acid. Diphenolic acid is an appropriate starting reactant since it is commercially readily available at low cost.

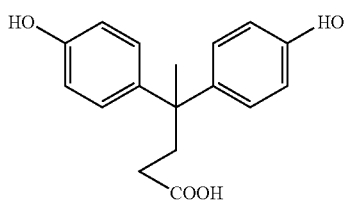

(12-9)

When the appropriate starting reactant, diphenolic acid is used, the resulting bis(4-hydroxy-3-allylphenyl) derivative having an alcoholic hydroxyl group is a compound represented by the following formula (7), which is most preferred for use in the "hydrosilylation" polymerization mentioned above.

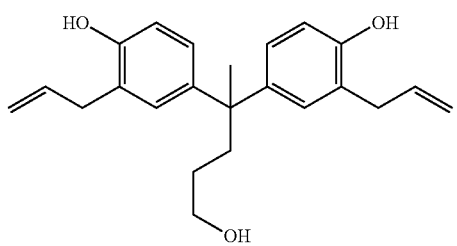

(7)

As described previously, the silicone structure-bearing polymer is readily obtained through hydrosilylation reaction of the bis(4-hydroxy-3-allylphenyl) derivative having an alcoholic hydroxyl group, represented by formula (6) with hydroxyl-containing organopolysiloxanes of formulae (8) and (9). The resulting silicone structure-bearing polymer having the structure represented by formula (1) is useful as a base resin in a chemically amplified negative resist composition because it substantially overcomes the stripping problem that can be encountered on wirings and electrodes of metal (e.g., Cu or Al), and substrates, typically SiN substrates. The stripping problem is solved probably because the structural moiety of formula (4) introduced in the silicone structure-bearing polymer facilitates interaction with the substrate. When a chemically amplified negative resist composition comprising a silicone structure-bearing polymer not having the structural moiety of formula (4) is used to form a pattern, the pattern substantially lacks adhesion to the substrate.

In contrast, as a result of introduction of the structural moiety of formula (4) in the silicone structure-bearing polymer, the polymer is improved in solubility in the organic solvent which is a developer for chemically amplified negative resist compositions. For the negative resist composition, a high solubility of the unexposed region in the developer is desirable. That is, in the step of resolving a fine size pattern, if the solubility of the unexposed region in the developer is low, sometimes undissolved residue (scum) is observed on the pattern bottom or footing is observed between the pattern and the substrate. When a pattern is formed using the chemically amplified negative resist composition comprising the inventive silicone structure-bearing polymer, the occurrence of scumming and footing at the pattern bottom is avoided because the solubility of the unexposed region in the organic solvent developer is improved.

Also when a pattern is formed using the chemically amplified negative resist composition comprising the inventive silicone structure-bearing polymer, the crosslinking reaction in the exposed region can be promoted. As the crosslinking reaction in the exposed region is promoted, the solubility of the exposed region in the organic solvent developer is reduced. The resist composition is successful in improving the solubility of the unexposed region in the developer as discussed previously and in substantially reducing the solubility of the exposed region in the developer, thus increasing the difference in dissolution rate between exposed and unexposed regions. Since the chemically amplified negative resist composition is significantly improved in dissolution contrast, formation of a finer size pattern is expectable.

Chemically Amplified Negative Resist Composition

Another embodiment of the invention is a chemically amplified negative resist composition comprising (A) the silicone structure-bearing polymer defined above, having a Mw of 3,000 to 500,000, (B) a photoacid generator which is decomposed to generate an acid upon exposure to radiation of wavelength 190 to 500 nm, (C) at least one crosslinker selected from the group consisting of an amino condensate modified with formaldehyde or formaldehyde-alcohol, a phenol compound having on the average at least two methylol or alkoxymethylol groups in the molecule, a polyhydric phenol compound in which at least one hydrogen atom of hydroxyl group is substituted by a glycidyl group, a polyhydric phenol compound in which at least one hydrogen atom of hydroxyl group is substituted by a group of the formula (C-1), and a compound containing at least two structures each having nitrogen bonded to a glycidyl group, the structure having the formula (C-2) or (C-3),

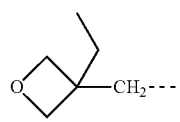 (C-1)

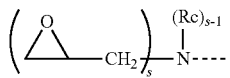 (C-2)

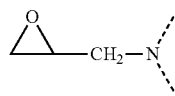 (C-3)

wherein the broken line segment denotes a valence bond, Rc is a straight, branched or cyclic $C_1$-$C_6$ alkyl group, and s is 1 or 2, and (D) a solvent.

The photoacid generator (B) is typically a compound which generates an acid upon exposure to light with a wavelength of 190 to 500 nm, the acid generated serving as a curing catalyst. Since the resist composition of the invention is highly compatible with the PAG, the PAG may be selected from a wide variety of such compounds. Typical PAGs include onium salts, diazomethane derivatives, glyoxime derivatives, β-ketosulfone derivatives, disulfone derivatives, nitrobenzyl sulfonate derivatives, sulfonic acid ester derivatives, imido-yl sulfonate derivatives, oxime sulfonate derivatives, imino sulfonate derivatives, and triazine derivatives.

Exemplary onium salts are compounds of the following general formula (13).

$$(R^{12})_j M^+ K^- \tag{13}$$

Herein, $R^{12}$ is a straight, branched or cyclic $C_1$-$C_{12}$ alkyl group, $C_6$-$C_{12}$ aryl group or $C_7$-$C_{12}$ aralkyl group, which may have a substituent; $M^+$ is iodonium or sulfonium; $K^-$ is a non-nucleophilic counter-ion; and j is 2 or 3.

Illustrative examples of alkyl groups represented by $R^{12}$ include methyl, ethyl, propyl, butyl, cyclohexyl, 2-oxocyclohexyl, norbornyl, and adamantyl. Exemplary aryl groups include phenyl; alkoxyphenyl groups such as o-, m- or p-methoxyphenyl, ethoxyphenyl, m- or p-tert-butoxyphenyl; and alkylphenyl groups such as 2-, 3- or 4-methylphenyl, ethylphenyl, 4-tert-butylphenyl, 4-butylphenyl, and dimethylphenyl. Exemplary aralkyl groups include benzyl and phenethyl.

Examples of the non-nucleophilic counter-ion represented by $K^-$ include halide ions such as chloride and bromide; fluoroalkylsulfonate ions such as triflate, 1,1,1-trifluoroethanesulfonate, and nonafluorobutanesulfonate; arylsulfonate ions such as tosylate, benzenesulfonate, 4-fluorobenzenesulfonate, and 1,2,3,4,5-pentafluorobenzenesulfonate; and alkylsulfonate ions such as mesylate and butanesulfonate.

Exemplary diazomethane derivatives are compounds of the following general formula (14).

 (14)

Herein, $R^{13}$, which may be the same or different, is a straight, branched or cyclic $C_1$-$C_{12}$ alkyl or haloalkyl group, $C_6$-$C_{12}$ aryl, alkoxyaryl, alkylaryl or haloaryl group, or $C_7$-$C_{12}$ aralkyl group.

Illustrative examples of alkyl groups represented by $R^{13}$ include methyl, ethyl, propyl, butyl, amyl, cyclopentyl, cyclohexyl, norbornyl, and adamantyl. Exemplary haloalkyl groups include trifluoromethyl, 1,1,1-trifluoroethyl, 1,1,1-trichloroethyl, and nonafluorobutyl. Exemplary aryl groups include phenyl; alkoxyphenyl groups such as o-, m- or p-methoxyphenyl, ethoxyphenyl, m- or p-tert-butoxyphenyl; and alkylphenyl groups such as 2-, 3- or 4-methylphenyl, ethylphenyl, 4-tert-butylphenyl, 4-butylphenyl, and dimethylphenyl. Exemplary haloaryl groups include fluorophenyl, chlorophenyl, and 1,2,3,4,5-pentafluorophenyl. Exemplary aralkyl groups include benzyl and phenethyl.

Illustrative examples of the PAG include:
onium salts such as diphenyliodonium trifluoromethanesulfonate, (p-tert-butoxyphenyl)phenyliodonium trifluoromethanesulfonate, diphenyliodonium p-toluenesulfonate, (p-tert-butoxyphenyl)phenyliodonium p-toluenesulfonate, triphenylsulfonium trifluoromethanesulfonate, (p-tert-butoxyphenyl)diphenylsulfonium trifluoromethanesulfonate, bis (p-tert-butoxyphenyl)phenylsulfonium trifluoromethanesulfonate, tris(p-tert-butoxyphenyl)sulfonium trifluoromethanesulfonate, triphenylsulfonium p-toluenesulfonate, (p-tert-butoxyphenyl)diphenylsulfonium p-toluenesulfonate, bis(p-tert-butoxyphenyl)phenylsulfonium p-toluenesulfonate, tris(p-tert-butoxyphenyl)sulfonium p-toluenesulfonate, triphenylsulfonium nonafluorobutanesulfonate, triphenylsulfonium butanesulfonate, trimethylsulfonium trifluoromethanesulfonate, trimethylsulfonium p-toluenesulfonate, cyclohexylmethyl(2-oxocyclohexyl)sulfonium trifluoromethanesulfonate, cyclohexylmethyl(2-oxocyclohexyl)sulfonium p-toluenesulfonate, dimethylphenylsulfonium trifluoromethanesulfonate, dimethylphenylsulfonium p-toluenesulfonate, dicyclohexylphenylsulfonium trifluoromethanesulfonate, dicyclohexylphenylsulfonium p-toluenesulfonate, and diphenyl(4-thiophenoxyphenyl)sulfonium hexafluoroantimonate;

diazomethane derivatives such as bis(benzenesulfonyl) diazomethane, bis(p-toluenesulfonyl)diazomethane, bis(xylenesulfonyl)diazomethane, bis(cyclohexylsulfonyl)diazomethane, bis(cyclopentylsulfonyl)diazomethane, bis(n-butylsulfonyl)diazomethane, bis(isobutylsulfonyl)diazomethane, bis(sec-butylsulfonyl)diazomethane, bis(n-propylsulfonyl)diazomethane, bis(isopropylsulfonyl)diazomethane, bis(tert-butylsulfonyl)diazomethane, bis(n-amylsulfonyl)diazomethane, bis(isoamylsulfonyl)diazomethane, bis(sec-amylsulfonyl)diazomethane, bis(tert-amylsulfonyl)diazomethane, 1-cyclohexylsulfonyl-1-(tert-butylsulfonyl)diazomethane, 1-cyclohexylsulfonyl-1-(tert-amylsulfonyl)diazomethane, and 1-tert-amylsulfonyl-1-(tert-butylsulfonyl)diazomethane;

glyoxime derivatives such as bis-O-(p-toluenesulfonyl)-α-dimethylglyoxime, bis-O-(p-toluenesulfonyl)-α-diphenylglyoxime, bis-O-(p-toluenesulfonyl)-α-dicyclohexylglyoxime, bis-O-(p-toluenesulfonyl)-2,3-pentanedioneglyoxime, bis-O-(p-toluenesulfonyl)-2-methyl-3,4-pentanedioneglyoxime, bis-O-(n-butanesulfonyl)-α-dimethylglyoxime, bis-O-(n-butanesulfonyl)-α-diphenylglyoxime, bis-O-(n-butanesulfonyl)-α-dicyclohexylglyoxime, bis-O-(n-butanesulfonyl)-2,3-pentanedioneglyoxime, bis-O-(n-butanesulfonyl)-2-methyl-3,4-pentanedioneglyoxime, bis-O-(methanesulfonyl)-α-dimethylglyoxime, bis-O-(trifluoromethanesulfonyl)-α-dimethylglyoxime, bis-O-(1,1,1-trifluoroethanesulfonyl)-α-dimethylglyoxime, bis-O-(tert-butanesulfonyl)-α-dimethylglyoxime, bis-O-(perfluorooctanesulfonyl)-α-dimethylglyoxime, bis-O-(cyclohexanesulfonyl)-α-dimethylglyoxime, bis-O-(benzenesulfonyl)-α-dimethylglyoxime, bis-O-(p-fluorobenzenesulfonyl)-α-dimethylglyoxime, bis-O-(p-tert-butylbenzenesulfonyl)-α-dimethylglyoxime, bis-O-(xylenesulfonyl)-α-dimethylglyoxime, and bis-O-(camphorsulfonyl)-α-dimethylglyoxime;

oxime sulfonate derivatives such as α-(benzenesulfoniumoxyimino)-4-methylphenylacetonitrile;

β-ketosulfone derivatives such as 2-cyclohexylcarbonyl-2-(p-toluenesulfonyl)propane and 2-isopropylcarbonyl-2-(p-toluenesulfonyl)propane;

disulfone derivatives such as diphenyl disulfone and dicyclohexyl disulfone; nitrobenzyl sulfonate derivatives such as 2,6-dinitrobenzyl p-toluenesulfonate and 2,4-dinitrobenzyl p-toluenesulfonate;

sulfonic acid ester derivatives such as 1,2,3-tris(methanesulfonyloxy)benzene, 1,2,3-tris(trifluoromethanesulfonyloxy)benzene, and 1,2,3-tris(p-toluenesulfonyloxy)benzene;

imido-yl sulfonate derivatives such as phthalimidoyl triflate, phthalimidoyl tosylate, 5-norbornene-2,3-dicarboxyimidoyl triflate, 5-norbornene-2,3-dicarboxyimidoyl tosylate, 5-norbornene-2,3-dicarboxyimidoyl n-butylsulfonate, and n-trifluoromethylsulfonyloxynaphthylimide;

iminosulfonates such as (5-(4-methylphenyl)sulfonyloxy-imino-5H-thiophen-2-ylidene)-(2-methylphenyl)acetonitrile and (5-(4-(4-methylphenylsulfonyloxy)phenylsulfonyloxy-imino)-5H-thiophen-2-ylidene)-(2-methylphenyl)acetonitrile, as well as 2-methyl-2[(4-methylphenyl)sulfonyl]-1-[(4-methylthio)phenyl]-1-propane.

Among others, imido-yl sulfonates, imino sulfonates and oxime sulfonates are preferred.

The PAGs may be used alone or in admixture of two or more. It is preferred from the standpoints of photo-absorption of the PAG itself and photo-curability of a thick film that the PAG be added in an amount of 0.05 to 20 parts by weight, and especially 0.2 to 5 parts by weight, per 100 parts by weight of the silicone structure-bearing polymer.

Component (C) is at least one crosslinker selected from the group consisting of an amino condensate modified with formaldehyde or formaldehyde-alcohol, a phenol compound having on the average at least two methylol or alkoxymethylol groups in the molecule, a polyhydric phenol compound in which at least one hydrogen atom of hydroxyl group is substituted by a glycidyl group, a polyhydric phenol compound in which at least one hydrogen atom of hydroxyl group is substituted by a group of the formula (C-1), and a compound containing at least two structures each having nitrogen bonded to a glycidyl group, the structure having the formula (C-2) or (C-3).

(C-1)

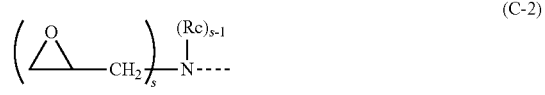

(C-2)

(C-3)

Herein Rc is a straight, branched or cyclic $C_1$-$C_6$ alkyl group, and s is 1 or 2.

The amino condensate modified with formaldehyde or formaldehyde-alcohol includes, for example, melamine condensates modified with formaldehyde or formaldehyde-alcohol, and urea condensates modified with formaldehyde or formaldehyde-alcohol.

The modified melamine condensates are prepared, for example, by modifying a melamine monomer with formaldehyde into a methylol form in a well-known manner, and optionally, further modifying it with an alcohol into an alkoxy form, thereby yielding a modified melamine of the general formula (15) shown below. The alcohols used herein are lower alcohols, for example, alcohols having 1 to 4 carbon atoms.

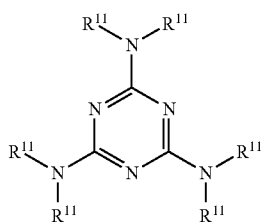

(15)

Herein, $R^{11}$, which may be the same or different, is a methylol group, an alkoxymethyl group containing a $C_1$-$C_4$ alkoxy moiety, or hydrogen, and at least one $R^{11}$ is a methylol or alkoxymethyl group. Specifically, $R^{11}$ is a methylol group, an alkoxymethyl group such as methoxymethyl or ethoxymethyl, or hydrogen.

Illustrative, non-limiting, examples of the modified melamine of formula (15) include trimethoxymethylmonomethylolmelamine, dimethoxymethylmonomethylolmelamine, trimethylolmelamine, hexamethylolmelamine, and hexamethoxymethylolmelamine.

Next, the modified melamine of formula (15) or an oligomer thereof (e.g., dimer or trimer) is subjected to addition condensation polymerization with formaldehyde in a customary way until a desired molecular weight is reached, thereby obtaining the formaldehyde or formaldehyde-alcohol-modified melamine condensate.

Also, the urea condensates modified with formaldehyde or formaldehyde-alcohol are prepared, for example, by modifying a urea condensate having a desired molecular weight with formaldehyde into a methylol form in a well-known manner, and optionally, further modifying it with an alcohol into an alkoxy form.

Illustrative examples of the modified urea condensate include methoxymethylated urea condensates, ethoxymethylated urea condensates, and propoxymethylated urea condensates. These modified melamine condensates and modified urea condensates may be used alone or in admixture of two or more.

Examples of the phenol compound having on the average at least two methylol or alkoxymethylol groups in a molecule include (2-hydroxy-5-methyl)-1,3-benzenedimethanol and 2,2',6,6'-tetramethoxymethylbisphenol A as well as compounds of the following formulae (C-4) to (C-8).

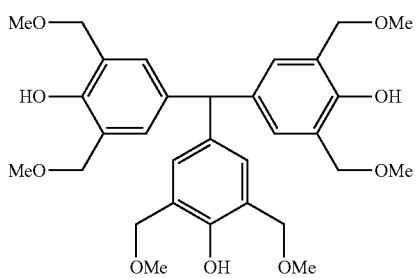
(C-4)

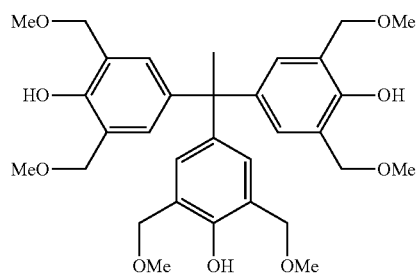
(C-5)

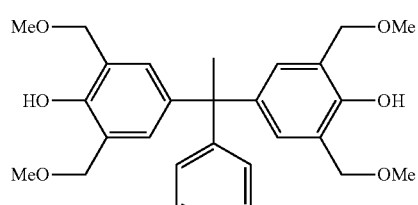
(C-6)

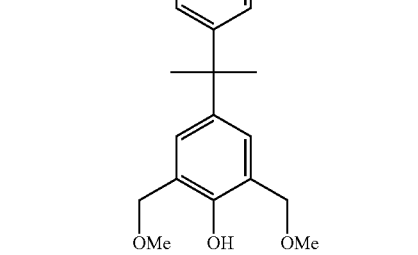
(C-7)

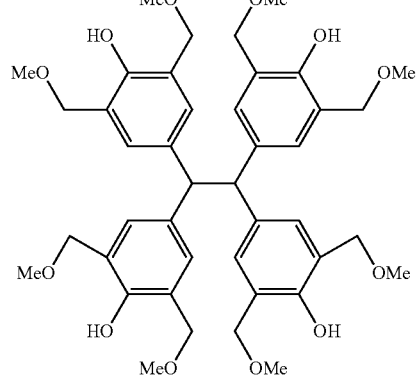

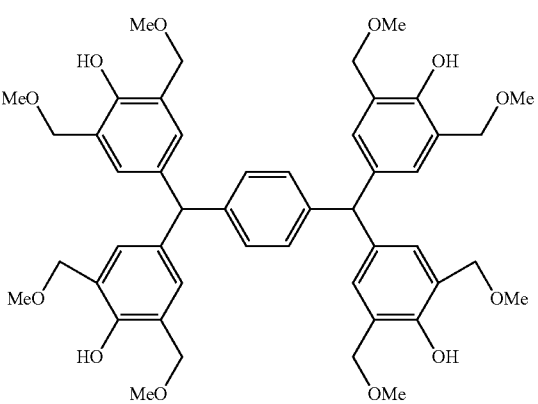
(C-8)

These phenol compounds may be used alone or in admixture of two or more as the crosslinker.

Examples of the polyhydric phenol compound having a hydroxyl group whose hydrogen is substituted by a glycidyl group include those compounds which are obtained by reacting hydroxyl groups of bisphenol A, tris(4-hydroxyphenyl) methane, and 1,1,1-tris(4-hydroxyphenyl)ethane with epichlorohydrin in the presence of a base. Preferred examples of the polyhydric phenol compound having a hydroxyl group whose hydrogen is substituted by a glycidyl group include compounds of the following formulae (C-9) to (C-15).

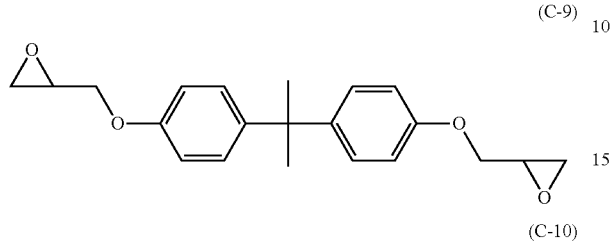

(C-9)

(C-10)

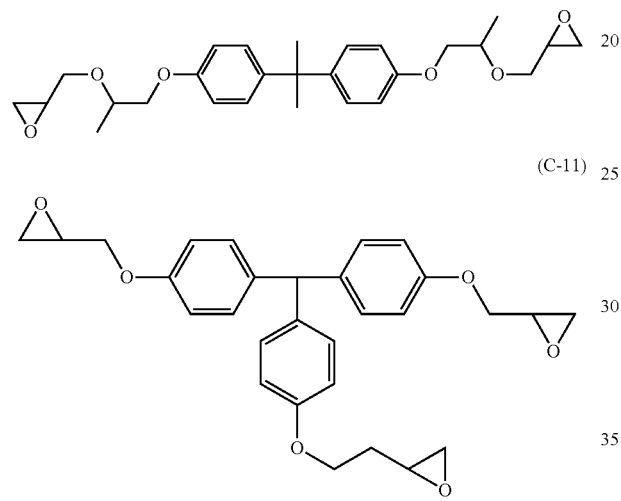

(C-11)

(C-12)

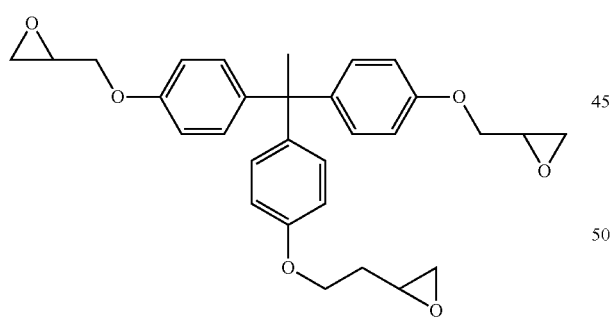

(C-13)

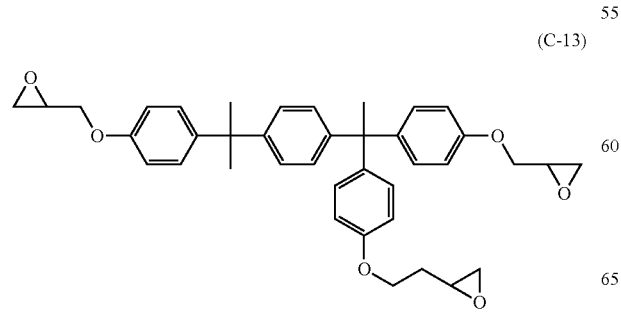

-continued

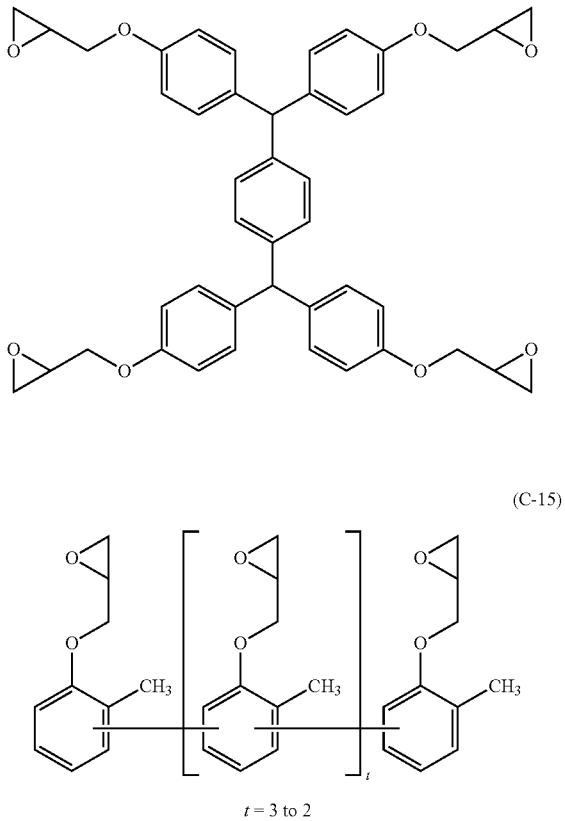

(C-14)

(C-15)

$t = 3$ to 2

These polyhydric phenol compounds having a hydroxyl group substituted by a glycidoxy group may also be used alone or in admixture of two or more as the crosslinker.

The compounds containing at least two groups of formula (C-1), (C-2) or (C-3) are preferably those compounds having 2 to 10 organic groups, more preferably 2 to 5 organic groups.

The substituent group of formula (C-1) is typically a group having the following formula (C-16).

(C-1)

(C-16)

$u = 1$ to 3

Typically the compound containing at least two structures each having nitrogen bonded to a glycidyl group, the structure having the formula (C-2) or (C-3) may be represented by the following formula (C-17).

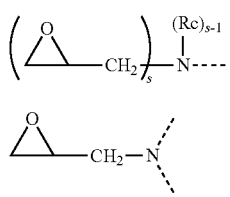
(C-2)

(C-3)

Herein Rc is a straight, branched or cyclic $C_1$-$C_6$ alkyl group, and s is 1 or 2.

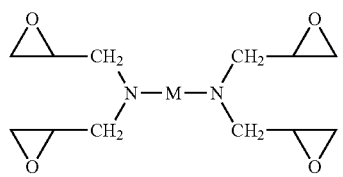
(C-17)

In formula (C-17), M is a divalent, straight, branched or cyclic $C_2$-$C_{12}$ alkylene group or aromatic group. Examples of the compound having formula (C-17) include compounds of the following formulae (C-18) to (C-21).

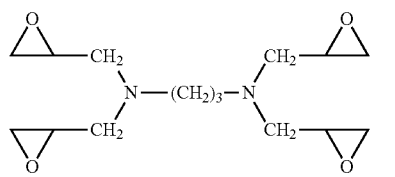
(C-18)

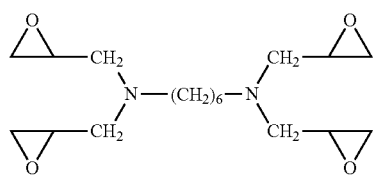
(C-19)

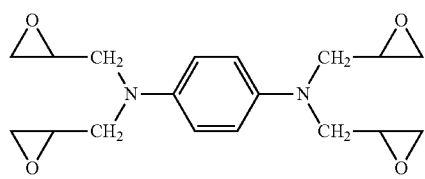
(C-20)

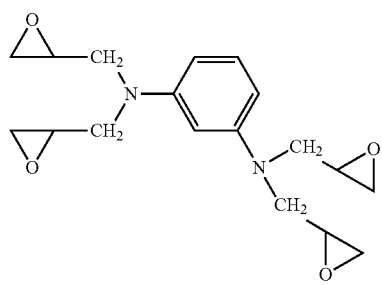
(C-21)

Typical of the compound containing at least two nitrogen-bonded glycidyl groups of formula (C-2) or (C-3) is a compound of the following formula (C-22).

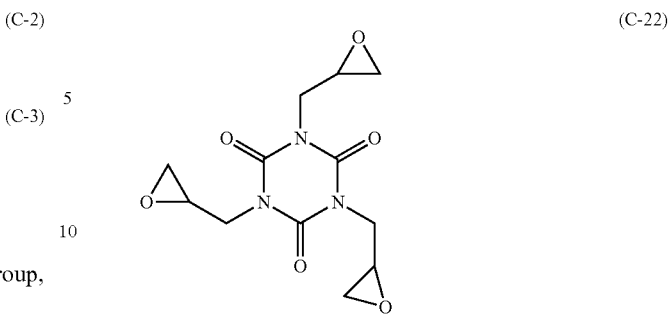
(C-22)

The compound containing at least two nitrogen-bonded glycidyl groups may also be used alone or in admixture of two or more as the crosslinker.

The crosslinker induces curing reaction with the silicone structure-bearing polymer for facilitating pattern formation and augmenting the strength of a cured product. The crosslinker should preferably have a weight average molecular weight (Mw) of 150 to 10,000, and more preferably 200 to 3,000, from the standpoints of photo-curability and heat resistance.

It is preferred from the standpoints of photo-curability and reliability of a protective film after post-curing that the crosslinker be used in an amount of 0.5 to 50 parts, and especially 1 to 30 parts by weight per 100 parts by weight of the silicone structure-bearing polymer (A).

The solvent (D) used herein may be any organic solvent in which the silicone structure-bearing polymer (A), PAG (B) and crosslinker (C) are soluble. Illustrative, non-limiting, examples of the organic solvent include ketones such as cyclohexanone, cyclopentanone and methyl-2-n-amylketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; and esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate, and γ-butyrolactone. These solvents may be used alone or in combinations of two or more thereof. Of these solvents, preferred are ethyl lactate, cyclohexanone, cyclopentanone, PGMEA, γ-butyrolactone, and mixtures thereof, in which the PAG is most soluble.

It is preferred from the standpoints of compatibility, viscosity and ease of coating of the resulting resist composition that the solvent (D) be used in an amount of 50 to 2,000 parts, and especially 100 to 1,000 parts by weight per 100 parts by weight of components (A) to (C) combined.

If desired, (E) a basic compound may be added to the resist composition. The basic compound used herein is preferably a compound capable of suppressing the rate of diffusion when the acid generated by the PAG diffuses within the resist film. The inclusion of the basic compound improves resolution, suppresses changes in sensitivity following exposure and reduces substrate and environment dependence, as well as improving the exposure latitude and the pattern profile.

Examples of the basic compound include primary, secondary, and tertiary aliphatic amines, mixed amines, aromatic amines, heterocyclic amines, nitrogen-containing compounds with carboxyl group, nitrogen-containing compounds with sulfonyl group, nitrogen-containing compounds with hydroxyl group, nitrogen-containing compounds with hydroxyphenyl group, alcoholic nitrogen-containing compounds, amide derivatives, imide derivatives, and compound of the general formula (18).

$$N(\alpha)_q(\beta)_{3-q} \qquad (18)$$

Herein, q is equal to 1, 2 or 3; side chain β is independently hydrogen or a straight, branched or cyclic $C_1$-$C_{20}$ alkyl group which may contain an ether bond or hydroxyl group; and side chain α is independently selected from substituent groups of the following general formulas (19) to (21), and two or three α's may bond together to form a ring.

(19)

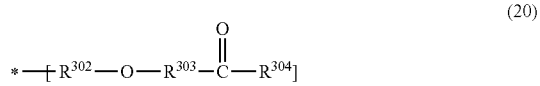

(20)

(21)

In the formulas, $R^{300}$, $R^{302}$ and $R^{305}$ are each independently a straight or branched $C_1$-$C_4$ alkylene group. $R^{301}$ and $R^{304}$ are each independently hydrogen, a straight, branched or cyclic $C_1$-$C_{20}$ alkyl group which may contain at least one hydroxyl group, ether bond, ester bond or lactone ring. $R^{303}$ is a single bond or a straight or branched $C_1$-$C_4$ alkylene group. $R^{306}$ is a straight, branched or cyclic $C_1$-$C_{20}$ alkyl group which may contain at least one hydroxyl group, ether bond, ester bond or lactone ring. The symbol * denotes the bonding terminal.

Examples of suitable primary aliphatic amines include ammonia, methylamine, ethylamine, n-propylamine, isopropylamine, n-butylamine, isobutylamine, sec-butylamine, tert-butylamine, pentylamine, tert-amylamine, cyclopentylamine, hexylamine, cyclohexylamine, heptylamine, octylamine, nonylamine, decylamine, dodecylamine, cetylamine, methylenediamine, ethylenediamine, and tetraethylenepentamine.

Examples of suitable secondary aliphatic amines include dimethylamine, diethylamine, di-n-propylamine, diisopropylamine, di-n-butylamine, diisobutylamine, di-sec-butylamine, dipentylamine, dicyclopentylamine, dihexylamine, dicyclohexylamine, diheptylamine, dioctylamine, dinonylamine, didecylamine, didodecylamine, dicetylamine, N,N-dimethylmethylenediamine, N,N-dimethylethylenediamine, and N,N-dimethyltetraethylenepentamine.

Examples of suitable tertiary aliphatic amines include trimethylamine, triethylamine, tri-n-propylamine, triisopropylamine, tri-n-butylamine, triisobutylamine, tri-sec-butylamine, tripentylamine, tricyclopentylamine, trihexylamine, tricyclohexylamine, triheptylamine, trioctylamine, trinonylamine, tridecylamine, tridodecylamine, tricetylamine, N,N,N',N'-tetramethylmethylenediamine, N,N,N',N'-tetramethylethylenediamine, and N,N,N',N'-tetramethyltetraethylenepentamine.

Examples of suitable mixed amines include dimethylethylamine, methylethylpropylamine, benzyl amine, phenethylamine, and benzyldimethylamine.

Examples of suitable aromatic and heterocyclic amines include aniline derivatives (e.g., aniline, N-methylaniline, N-ethylaniline, N-propylaniline, N,N-dimethylaniline, 2-methylaniline, 3-methylaniline, 4-methylaniline, ethylaniline, propylaniline, trimethylaniline, 2-nitroaniline, 3-nitroaniline, 4-nitroaniline, 2,4-dinitroaniline, 2,6-dinitroaniline, 3,5-dinitroaniline, and N,N-dimethyltoluidine), diphenyl(p-tolyl)amine, methyldiphenylamine, triphenylamine, phenylenediamine, naphthylamine, diaminonaphthalene, pyrrole derivatives (e.g., pyrrole, 2H-pyrrole, 1-methylpyrrole, 2,4-dimethylpyrrole, 2,5-dimethylpyrrole, and N-methylpyrrole), oxazole derivatives (e.g., oxazole and isooxazole), thiazole derivatives (e.g., thiazole and isothiazole), imidazole derivatives (e.g., imidazole, 4-methylimidazole, and 4-methyl-2-phenylimidazole), pyrazole derivatives, furazan derivatives, pyrroline derivatives (e.g., pyrroline and 2-methyl-1-pyrroline), pyrrolidine derivatives (e.g., pyrrolidine, N-methylpyrrolidine, pyrrolidinone, and N-methylpyrrolidone), imidazoline derivatives, imidazolidine derivatives, pyridine derivatives (e.g., pyridine, methylpyridine, ethylpyridine, propylpyridine, butylpyridine, 4-(1-butylpentyl)pyridine, dimethylpyridine, trimethylpyridine, triethylpyridine, phenylpyridine, 3-methyl-2-phenylpyridine, 4-tert-butylpyridine, diphenylpyridine, benzylpyridine, methoxypyridine, butoxypyridine, dimethoxypyridine, 1-methyl-2-pyridine, 4-pyrrolidinopyridine, 1-methyl-4-phenylpyridine, 2-(1-ethylpropyl)pyridine, aminopyridine, and dimethylaminopyridine), pyridazine derivatives, pyrimidine derivatives, pyrazine derivatives, pyrazoline derivatives, pyrazolidine derivatives, piperidine derivatives, piperazine derivatives, morpholine derivatives, indole derivatives, isoindole derivatives, 1H-indazole derivatives, indoline derivatives, quinoline derivatives (e.g., quinoline and 3-quinolinecarbonitrile), isoquinoline derivatives, cinnoline derivatives, quinazoline derivatives, quinoxaline derivatives, phthalazine derivatives, purine derivatives, pteridine derivatives, carbazole derivatives, phenanthridine derivatives, acridine derivatives, phenazine derivatives, 1,10-phenanthroline derivatives, adenine derivatives, adenosine derivatives, guanine derivatives, guanosine derivatives, uracil derivatives, and uridine derivatives.

Examples of suitable nitrogen-containing compounds with carboxyl group include aminobenzoic acid, indolecarboxylic acid, and amino acid derivatives (e.g. nicotinic acid, alanine, alginine, aspartic acid, glutamic acid, glycine, histidine, isoleucine, glycylleucine, leucine, methionine, phenylalanine, threonine, lysine, 3-aminopyrazine-2-carboxylic acid, and methoxyalanine).

Examples of suitable nitrogen-containing compounds with sulfonyl group include 3-pyridinesulfonic acid and pyridinium p-toluenesulfonate.

Examples of suitable nitrogen-containing compounds with hydroxyl group, nitrogen-containing compounds with hydroxyphenyl group, and alcoholic nitrogen-containing compounds include 2-hydroxypyridine, aminocresol, 2,4-quinolinediol, 3-indolemethanol hydrate, monoethanolamine, diethanolamine, triethanolamine, N-ethyldiethanolamine, N,N-diethylethanolamine, triisopropanolamine, 2,2'-iminodiethanol, 2-aminoethanol, 3-amino-1-propanol, 4-amino-1-butanol, 4-(2-hydroxyethyl)morpholine, 2-(2-hydroxyethyl)pyridine, 1-(2-hydroxyethyl)piperazine, 1-[2-(2-hydroxyethoxy)ethyl]piperazine, piperidine ethanol, 1-(2-hydroxyethyl)pyrrolidine, 1-(2-hydroxyethyl)-2-pyrrolidinone, 3-piperidino-1,2-propanediol, 3-pyrrolidino-1,2-propanediol, 8-hydroxyjulolidine, 3-quinuclidinol, 3-tropanol, 1-methyl-2-pyrrolidine ethanol, 1-aziridine ethanol, N-(2-hydroxyethyl)phthalimide, and N-(2-hydroxyethyl)isonicotinamide.

Examples of suitable amide derivatives include formamide, N-methylformamide, N,N-dimethylformamide, acetamide, N-methylacetamide, N,N-dimethylacetamide, propionamide, and benzamide.

Suitable imide derivatives include phthalimide, succinimide, and maleimide.

Examples of the compounds of formula (18) include tris[2-(methoxymethoxy)ethyl]amine, tris[2-(2-methoxyethoxy)ethyl]amine, tris[2-(2-methoxyethoxymethoxy)ethyl]amine, tris[2-(1-methoxyethoxy)ethyl]amine, tris[2-(1-ethoxyethoxy)ethyl]amine, tris[2-(1-ethoxypropoxy)ethyl]amine, tris[2-{2-(2-hydroxyethoxy)ethoxy}ethyl]amine, 4,7,13,16,21,24-hexaoxa-1,10-diazabicyclo[8.8.8]hexacosane, 4,7,13,18-tetraoxa-1,10-diazabicyclo[8.5.5]eicosane, 1,4,10,13-tetraoxa-7,16-diazabicyclooctadecane, 1-aza-12-crown-4,1-aza-15-crown-5,1-aza-18-crown-6, tris(2-formyloxyethyl)amine, tris(2-acetoxyethyl)amine, tris(2-propionyloxyethyl)amine, tris(2-butyryloxyethyl)amine, tris(2-isobutyryloxyethyl)amine, tris(2-valeryloxyethyl)amine, tris(2-pivaloyloxyethyl)amine, N,N-bis(2-acetoxyethyl)-2-(acetoxyacetoxy)ethylamine, tris(2-methoxycarbonyloxyethyl)amine, tris(2-tert-butoxycarbonyloxyethyl)amine, tris[2-(2-oxopropoxy)ethyl]amine, tris[2-(methoxycarbonylmethoxy)oxyethyl]amine, tris[2-(tert-butoxycarbonylmethyloxy)ethyl]amine, tris[2-(cyclohexyloxycarbonylmethyloxy)ethyl]amine, tris(2-methoxycarbonylethyl)amine, tris(2-ethoxycarbonylethyl)amine, N,N-bis(2-hydroxyethyl)-2-(methoxycarbonyl)ethylamine, N,N-bis(2-acetoxyethyl)-2-(methoxycarbonyl)ethylamine, N,N-bis(2-hydroxyethyl)-2-(ethoxycarbonyl)ethylamine, N,N-bis(2-acetoxyethyl)-2-(ethoxycarbonyl)ethylamine, N,N-bis(2-hydroxyethyl)-2-(2-methoxyethoxycarbonyl)ethylamine, N,N-bis(2-acetoxyethyl)-2-(2-methoxyethoxycarbonyl)ethylamine, N,N-bis(2-hydroxyethyl)-2-(2-hydroxyethoxycarbonyl)ethylamine, N,N-bis(2-acetoxyethyl)-2-(2-acetoxyethoxycarbonyl)ethylamine, N,N-bis(2-hydroxyethyl)-2-[(methoxycarbonyl)methoxycarbonyl]-ethylamine, N,N-bis(2-acetoxyethyl)-2-[(methoxycarbonyl)methoxycarbonyl]-ethylamine, N,N-bis(2-hydroxyethyl)-2-(2-oxopropoxycarbonyl)ethylamine, N,N-bis(2-acetoxyethyl)-2-(2-oxopropoxycarbonyl)ethylamine, N,N-bis(2-hydroxyethyl)-2-(tetrahydrofurfuryloxycarbonyl)-ethylamine, N,N-bis(2-acetoxyethyl)-2-(tetrahydrofurfuryloxycarbonyl)-ethylamine, N,N-bis(2-hydroxyethyl)-2-[(2-oxotetrahydrofuran-3-yl)oxy-carbonyl]ethylamine, N,N-bis(2-acetoxyethyl)-2-[(2-oxotetrahydrofuran-3-yl)oxy-carbonyl]ethylamine, N,N-bis(2-hydroxyethyl)-2-(4-hydroxybutoxycarbonyl)ethylamine, N,N-bis(2-formyloxyethyl)-2-(4-formyloxybutoxycarbonyl)-ethylamine, N,N-bis(2-formyloxyethyl)-2-(2-formyloxyethoxycarbonyl)-ethylamine, N,N-bis(2-methoxyethyl)-2-(methoxycarbonyl)ethylamine, N-(2-hydroxyethyl)bis[2-(methoxycarbonyl)ethyl]amine, N-(2-acetoxyethyl)bis[2-(methoxycarbonyl)ethyl]amine, N-(2-hydroxyethyl)bis[2-(ethoxycarbonyl)ethyl]amine, N-(2-acetoxyethyl)bis[2-(ethoxycarbonyl)ethyl]amine, N-(3-hydroxy-1-propyl)bis[2-(methoxycarbonyl)ethyl]amine, N-(3-acetoxy-1-propyl)bis[2-(methoxycarbonyl)ethyl]amine, N-(2-methoxyethyl)bis[2-(methoxycarbonyl)ethyl]amine, N-butylbis[2-(methoxycarbonyl)ethyl]amine, N-butylbis[2-(2-methoxyethoxycarbonyl)ethyl]amine, N-methylbis(2-acetoxyethyl)amine, N-ethylbis(2-acetoxyethyl)amine, N-methylbis(2-pivaloyloxyethyl)amine, N-ethylbis[2-(methoxycarbonyloxy)ethyl]amine, N-ethylbis[2-(tert-butoxycarbonyloxy)ethyl]amine, tris(methoxycarbonylmethyl)amine, tris(ethoxycarbonylmethyl)amine, N-butylbis(methoxycarbonylmethyl)amine, N-hexylbis(methoxycarbonylmethyl)amine, and β-(diethylamino)-δ-valerolactone.

The basic compounds may be used alone or in admixture of two or more. From the standpoint of sensitivity, the basic compound may be formulated in an amount of 0 to 3 parts, and preferably 0.01 to 1 part by weight per 100 parts by weight of the silicone structure-bearing polymer.

In addition to the aforementioned components, the resist composition may include optional components. Suitable additives include a surfactant which is commonly used for improving the coating characteristics, and a light absorber which is commonly used for improving light absorption efficiency of photoacid generators or the like.

Preferred surfactants are nonionic surfactants, for example, fluorochemical surfactants such as perfluoroalkyl polyoxyethylene ethanols, fluorinated alkyl esters, perfluoroalkylamine oxides, and fluorinated organosiloxane compounds. These surfactants are commercially available. Illustrative examples include Fluorad FC-4430 from Sumitomo 3M Ltd., Surflon S-141 and S-145 from Asahi Glass Co., Ltd., Unidyne DS-401, DS-4031, and DS-451 from Daikin Industries Ltd., Megaface F-8151 from DIC Corp., and X-70-093 from Shin-Etsu Chemical Co., Ltd. Preferred surfactants include Fluorad FC-4430 from Sumitomo 3M Ltd. and X-70-093 from Shin-Etsu Chemical Co., Ltd.

Exemplary light absorbers include diaryl sulfoxides, diaryl sulfones, 9,10-dimethylanthracene and 9-fluorenone.

The chemically amplified negative resist composition of the invention is prepared in a conventional way. For example, it can be prepared by agitating and mixing the aforementioned components and optional additives in the solvent and passing the mixture through a filter. When a dry film to be described later is manufactured, a resist composition which is similarly prepared may be used.

Pattern Forming Process

A further embodiment is a pattern forming process using the chemically amplified negative resist composition defined above. Any well-known lithography may be used in forming a pattern using the negative resist composition. Specifically, the resist composition is applied onto a substrate such as silicon wafer, $SiO_2$ substrate or SiN substrate or a substrate having a pattern (e.g., copper wirings) formed thereon, by a well-known technique, typically spin coating, and prebaked at 80 to 130° C. for 50 to 600 seconds to form a resist film having a thickness of 1 to 50 μm, preferably 1 to 30 μm, and more preferably 5 to 20 μm. Then a mask having the desired pattern is placed above the resist film, which is exposed to high-energy radiation having a wavelength of 190 to 500 nm, typically i- or g-line, in a dose of 1 to 5,000 mJ/cm$^2$, preferably 100 to 2,000 mJ/cm$^2$. This may be followed by bake (PEB) on a hot plate at 60 to 150° C. for 1 to 10 minutes, preferably at 80 to 120° C. for 1 to 5 minutes. As a result of exposure, an insolubilized pattern is formed in which the exposed region of resist film is crosslinked and becomes insoluble in a solvent as developer.

Following the exposure or exposure and PEB, the resist film is developed in a developer. The developer may be the solvent used in the preparation of the chemically amplified negative resist composition. Suitable solvents include alcohols such as isopropyl alcohol (IPA), ketones such as cyclohexanone, and glycols such as propylene glycol monomethyl ether. Development is effected in a conventional manner, for example, by dipping the pattern-bearing substrate in the developer. The development is followed by washing, rinsing and drying if necessary. There is obtained a resist coating having the desired pattern. Although the pattern forming process has been described, it is sometimes unnecessary to form a pattern. When it is simply desired to form a uniform film, for example, the same process as above may be followed except that the photomask is not used.

If desired, the patterned coating may be post-cured by heating in an oven or hot plate at 100 to 250° C., preferably 150 to 220° C., and more preferably 170 to 190° C. Post-curing at a temperature of 100 to 250° C. is effective for increasing the crosslinking density of the resist coating and removing the residual volatile matter. Then a coating having augmented adhesion to substrates, heat resistance, high strength and good electrical properties can be formed. The post-curing time may range from 10 minutes to 10 hours.

Since the cured coating obtained in the above-described way has flexibility, substrate adhesion, heat resistance, electrical properties, mechanical properties, and chemical resistance in solder flux fluids, it can be advantageously used as a protective film on electric and electronic components and semiconductor devices. Semiconductor devices covered with the protective films remain reliable. In a thermal cycling test of the protective films, no cracks form.

Photo-Curable Dry Film

Using the resist composition, a photo-curable dry film may be manufactured. A further embodiment of the invention is a photo-curable dry film comprising a photo-curable resin layer sandwiched between a support film and a protective film.

First, the structure of the photo-curable dry film is described. The photo-curable dry film includes a support film, a protective film, and a photo-curable resin layer sandwiched therebetween. The photo-curable resin layer is formed of the resist composition which is suitable for forming an electric/electronic part-protecting film. The photo-curable dry film enables to form a fine size pattern over a wide range of film thickness and wavelength, and post-cure at low temperature leads to improvements in flexibility, heat resistance, electric properties, adhesion, reliability and chemical resistance.

The photo-curable resin layer in the photo-curable dry film is solid. Since the photo-curable resin layer is solventless, it eliminates the risk that bubbles resulting from volatilization of a solvent are left within the resin layer and between the resin layer and the rugged substrate surface. Although the advancement of semiconductor devices toward small size, thin profile and multilayer stacking brings in the tendency that the interlayer dielectric layer to which the invention is applicable is thinner, an appropriate thickness range exists for the layer when planarity and step coverage on rugged substrate surface are taken into account. Accordingly, from the standpoints of planarity and step coverage, the photo-curable resin layer should have a thickness of 10 to 100 µm, preferably 10 to 70 µm, and more preferably 10 to 50 µm.

Further, the viscosity and fluidity of the photo-curable resin layer are closely correlated. That is, the photo-curable resin layer within a proper viscosity range exhibits a sufficient fluidity to fill deeply even in a narrow gap.

Accordingly, the photo-curable dry film has the advantage that when tightly attached to a substrate having asperities on its surface, the photo-curable resin layer is coated so as to conform to the asperities, achieving high planarity. Particularly because the photo-curable resin layer is composed mainly of a photo-curable silicone composition, higher planarity is achievable owing to the advantage of low surface tension. Further, if the photo-curable resin layer is brought in close contact with the substrate in a vacuum environment, generation of gaps therebetween is effectively inhibited.

Now the method for manufacturing the photo-curable dry film and the pattern forming process using the photo-curable dry film are described.

In the photo-curable dry film, the chemically amplified negative resist composition used to form the photo-curable resin layer may be prepared as described above, specifically by combining the selected components, stirring, and filtering through a filter, thus yielding a photo-curable resin layer-forming material.

The support film used in the photo-curable dry film may be a single film or a multilayer film consisting of a plurality of stacked polymer layers. Examples of the film material include synthetic resins such as polyethylene, polypropylene, polycarbonate and polyethylene terephthalate (PET), with the PET film being preferred for appropriate flexibility, mechanical strength and heat resistance. These films may have been pretreated such as by corona treatment or coating of a release agent. Such films are commercially available, for example, Cerapeel® WZ(RX) and Cerapeel® BX8(R) from Toray Advanced Film Co., Ltd.; E7302 and E7304 from Toyobo Co., Ltd.; Purex® G31 and Purex® G71T1 from Teijin DuPont Films Japan Ltd.; and PET38×1-A3, PET38×1-V8 and PET38×1-X08 from Nippa Co., Ltd.

The protective film used in the photo-curable dry film may be similar to the support film. Among others, PET and polyethylene films having an appropriate flexibility are preferred. Such films are also commercially available. For example, PET films are as mentioned above, and polyethylene films include GF-8 from Tamapoly Co., Ltd. and PE film 0 type from Nippa Co., Ltd.

Both the support and protective films preferably have a thickness of 10 to 100 µm, more preferably 25 to 50 µm, for consistent manufacture of photo-curable dry film, and prevention of wrapping on a take-up roll, i.e., anti-curling.

Next, it is described how to manufacture the photo-curable dry film. An apparatus for manufacturing the photo-curable dry film may be a film coater commonly used in the manufacture of pressure-sensitive adhesive products. Suitable film coaters include, for example, a comma coater, comma reverse coater, multiple coater, die coater, lip coater, lip reverse coater, direct gravure coater, offset gravure coater, three-roll bottom reverse coater, and four-roll bottom reverse coater.

The support film is unwound from a supply roll in the film coater, passed across the head of the film coater where the resist composition is coated onto the support film to the predetermined buildup, and then moved through a hot air circulating oven at a predetermined temperature for a predetermined time, where the photo-curable resin layer is dried on the support film. Thereafter, the support film having the photo-curable resin layer thereon and a protective film which is unwound from another supply roll in the film coater are passed across a laminate roll under a predetermined pressure whereby the protective film is bonded to the photo-curable resin layer on the support film, whereupon the laminate is wound up on a take-up shaft in the film coater. Preferably, the oven temperature is 25 to 150° C., the time is 1 to 100 minutes, and the bonding pressure is 0.01 to 5 MPa.

Further, the pattern forming process using the photo-curable dry film is described. The process involves the steps of stripping the protective film from the photo-curable dry film, placing the bare photo-curable resin layer in close contact with a substrate, exposing the photo-curable resin layer to radiation, bake (PEB), developing and optionally post-curing to form a pattern of the layer. In this way, a protective film for electric and electronic parts is obtained.

Specifically, the photo-curable dry film is first placed in close contact with a substrate using a film attachment apparatus. The substrate used herein may be selected from silicon wafers, TSV silicon wafers, plastic, ceramic and metallic circuit boards. A typical substrate is provided with holes or grooves having an opening width of 10 to 100 μm and a depth of 10 to 120 μm. The film attachment apparatus is preferably a vacuum laminator. The photo-curable dry film is mounted in the film attachment apparatus where the protective film is stripped from the dry film. In the vacuum chamber kept at a predetermined vacuum, the bare photo-curable resin layer of the dry film is closely bonded to the substrate on a table at a predetermined temperature, using a bonding roll under a predetermined pressure. Preferably, the temperature is 60 to 120° C., the pressure is 0 to 5.0 MPa, and the vacuum is 50 to 500 Pa. After bonding, any well-known lithography may be performed to form a pattern.

At this point, the assembly of the photo-curable resin layer on the substrate may be prebaked, if necessary, for facilitating photo-cure reaction of the photo-curable resin layer or enhancing the adhesion between the photo-curable resin layer and the substrate. Prebake may be, for example, at 40 to 140° C. for 1 minute to 1 hour. Next, the photo-curable resin layer, with the support film or with the support film stripped off, is exposed to radiation of wavelength 190 to 500 nm through a photomask. The photomask may be, for example, a mask with a desired pattern perforated. The material of the photomask is preferably capable of cutting off radiation of wavelength 190 to 500 nm. For example, chromium or the like is preferably used, but the mask material is not limited thereto. The radiation of wavelength 190 to 500 nm includes radiation of various wavelengths emitted by a radiation emitter, for example, UV radiation such as g and i-lines, and deep UV radiation (193 nm and 248 nm). The preferred wavelength is from 248 nm to 436 nm. The exposure dose is preferably 10 to 3,000 mJ/cm$^2$, for example. Through this exposure, the exposed region is crosslinked and insolubilized in a developer, forming an insolubilized pattern. To enhance the development sensitivity, the layer may be baked (PEB). The PEB may be, for example, 40 to 140° C. for 0.5 to 10 minutes.

This is followed by development in a developer. The developer used herein may be the solvent for the resist composition used in the formation of the photo-curable resin layer in the photo-curable dry film. The developer is preferably selected from alcohols such as isopropyl alcohol (IPA), ketones such as cyclohexanone, and glycols such as propylene glycol monomethyl ether. The development may be carried out in a conventional manner, for example, by immersing the resin layer-bearing substrate in the developer. This is followed by optional cleaning, rinsing and drying, obtaining a film in the form of the photo-curable resin layer having the desired pattern. Where a pattern need not be formed, for example, merely a uniform film is to be formed, the same procedure as the above pattern forming procedure may be employed except that the photomask is not used.

Further, the patterned layer may be post-cured by heating in an oven or on a hot plate at a temperature of 100 to 250° C., preferably 150 to 220° C., and more preferably 170 to 190° C. The post-cure temperature of 100 to 250° C. is sufficient to increase the crosslinking density of the layer of the photo-curable resin composition, to remove any residual volatiles, and to enhance adhesion to substrate, heat resistance, strength, and electric properties. The post-cure time may be 10 minutes to 10 hours.

The thus cured film also possesses flexibility, adhesion to substrate, heat resistance, electric properties, mechanical strength, and resistance to chemicals, typically solder flux. When used as protective film, the cured film provides semiconductor devices with reliability and prevents crack formation in a thermal cycling test. The cured film is thus best suited as protective film for electric and electronic parts, semiconductor devices, and the like.

The dry film is advantageously applicable to substrates having grooves and holes. Thus the invention also provides a laminate comprising a substrate provided with grooves and/or holes having an opening width of 10 to 100 μm and a depth of 10 to 120 μm, and a layer lying on the substrate, the layer being a cured layer of the photo-curable resin composition extracted from the photo-curable dry film defined above.

EXAMPLE

Synthesis Examples, Examples and Comparative Examples are given below by way of illustration and not by way of limitation. All parts are by weight (pbw).

I. Preparation of Chemically Amplified Negative Resist Composition

In Synthesis Examples below, compounds M-1 to M-9 having the chemical structure shown below were used.

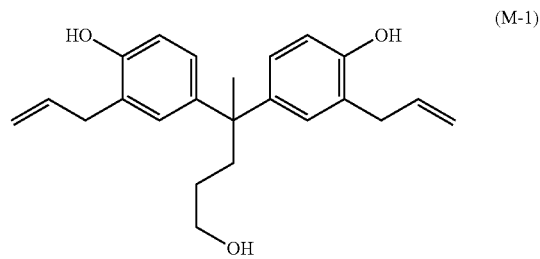

(M-1)

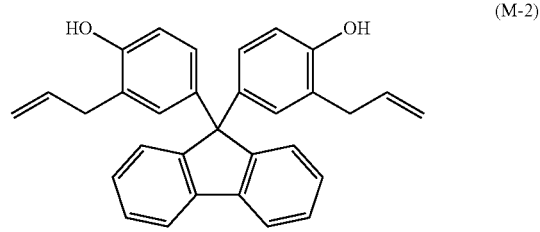

(M-2)

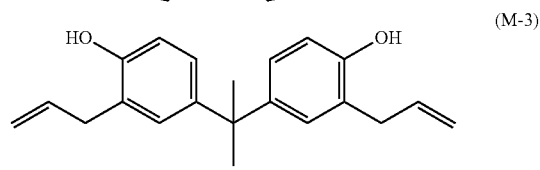

(M-3)

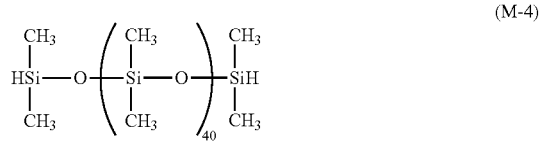

(M-4)

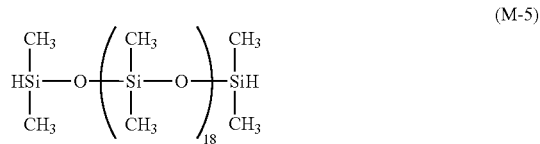

(M-5)

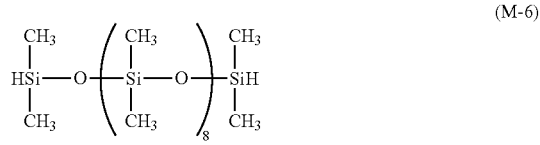

(M-6)

(M-7)

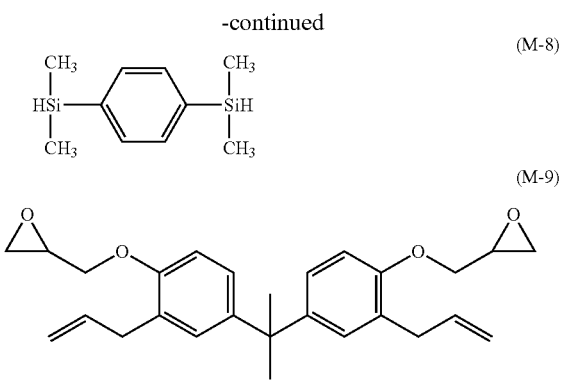

(M-8)

(M-9)

Synthesis Example 1

Synthesis of 4,4-bis(4-hydroxy-3-allylphenyl)pentanol (M-1)

A 5-L flask equipped with a stirrer, thermometer, and nitrogen purging line was charged with 458 g of diphenolic acid, 884 g of potassium carbonate, and 2,000 g of dimethylacetamide. With stirring in a nitrogen atmosphere at room temperature, 774 g of allyl bromide was added dropwise, followed by stirring at 60° C. for 58 hours. With the temperature kept, 221 g of potassium carbonate, 193 g of allyl bromide and 500 g of dimethylacetamide were added, followed by stirring at 60° C. for 20 hours. Under ice cooling, 2,000 g of water was added dropwise to quench the reaction. Then 1,000 g of toluene, 1,000 g of hexane, and 2,000 g of water were added to the reaction solution, from which an organic layer was taken out. The organic layer was sequentially washed with 2,000 g of water, four 500-g portions of water, and 500 g of saturated saline solution. Thereafter the solvent was distilled off, obtaining 686 g of allyl 4,4-bis(4-allyloxyphenyl)pentanoate in crude form.

A 5-L flask equipped with a stirrer, thermometer, and nitrogen purging line was charged with 655 g of allyl 4,4-bis(4-allyloxyphenyl)pentanoate and 1,310 g of tetrahydrofuran in a nitrogen atmosphere. Under ice cooling, 605 g of 70 wt % toluene solution of sodium bis(2-methoxyethoxy)aluminumhydride was added dropwise to the solution, followed by stirring at room temperature for 3 hours. Under ice cooling, 1,526 g of 10 wt % hydrochloric acid aqueous solution was added dropwise to quench the reaction. To the reaction solution were added 250 g of ethyl acetate and 750 g of toluene. An organic layer was taken out and washed three times with 500 g of water. The solvent was distilled off from the organic layer, and the residue was dissolved in 1,000 g of toluene, which was sequentially washed with five 300-g portions of 4 wt % sodium hydroxide aqueous solution, 330 g of 2 wt % hydrochloric acid aqueous solution, and four 300-g portions of water. Thereafter, the solvent was distilled off from the organic layer, obtaining 555 g of 4,4-bis(4-allyloxyphenyl) pentanol in crude form.

A 5-L flask equipped with a stirrer, thermometer, and nitrogen purging line was charged with 500 g of 4,4-bis(4-allyloxyphenyl)pentanol and 500 g of N,N-diethylaniline in a nitrogen atmosphere. The solution was heated and stirred at 180° C. for 18 hours, after which it was cooled down to room temperature. Under ice cooling, 1,460 g of 10 wt % hydrochloric acid aqueous solution was added dropwise to the reaction solution, and 2,400 g of ethyl acetate added thereto. An organic layer was taken out and washed four times with 2,400 g of water. The solvent was distilled off from the organic layer. The residue was dissolved in 500 g of ethyl acetate, which was stirred while 2,000 g of hexane was added dropwise. The hexane layer was removed, and the oily residue was dissolved in 500 g of ethyl acetate. From the organic layer, the solvent was distilled off, obtaining 466 g of 4,4-bis(4-hydroxy-3-allylphenyl)pentanol, M-1 in a yield of 93%. The compound M-1 was identified by $^1$H-NMR spectroscopy at 600 MHz (JEOL-600 by JEOL Ltd.).

Synthesis Example 2

Synthesis of Silicone Structure-Bearing Polymer Solution (A-1)

In a 3-L flask equipped with a stirrer, thermometer, nitrogen purging line and reflux condenser, 139.5 g of compound M-1 was dissolved in 750 g of toluene. To the solution, 208.7 g of compound M-4 and 2.4 g of compound M-7 were added, and it was heated at 60° C. To the flask, 0.9 g of platinum-on-carbon catalyst (5 wt %) was admitted whereupon the internal reaction temperature rose to 65-67° C. After confirmation of this temperature rise, the flask was heated at 90° C. for 1 hour and cooled to 60° C. again. To the flask, 0.9 g of platinum-on-carbon catalyst (5 wt %) was admitted, and 50.1 g of compound M-8 was added dropwise over 1 hour. At this point, the flask internal temperature rose to 65-67° C. After the dropwise addition, the reaction solution was ripened for 3 hours at 90° C., then cooled to 60° C., and ripened for 8 days. In the 8-day ripening course, each 1.8 g of platinum-on-carbon catalyst (5 wt %) was admitted on the 2nd, 3rd, 4th, 7th and 8th days. To the reaction solution was added 700 g of methyl isobutyl ketone. The reaction solution was filtered through a filter under pressure to remove the platinum catalyst. To the silicone structure-bearing polymer solution thus obtained, 300 g of deionized water was added, followed by stirring and stationary holding for separation. The lower layer or water layer was removed. This washing/separatory operation was repeated 6 times, thereby removing the trace acid value from the silicone structure-bearing polymer solution. The solvent was distilled off in vacuum from the silicone structure-bearing polymer solution and instead, 700 g of cyclopentanone was added. The solution was concentrated in vacuum, yielding a silicone structure-bearing polymer solution (A-1) in cyclopentanone having a resin solids concentration of 65-70 wt %. The silicone structure-bearing polymer in the solution was measured for molecular weight by GPC versus polystyrene standards, finding a Mw of 28,000. The polymer corresponded to formula (1) wherein molar fractions a=0, b=0, c=0, d=0, e=0.744, and f=0.256. W is as shown below.

W = 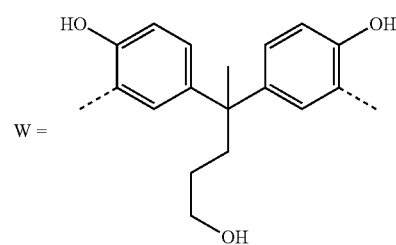

Synthesis Example 3

Synthesis of Silicone Structure-Bearing Polymer Solution (A-2)

In a 3-L flask equipped with a stirrer, thermometer, nitrogen purging line and reflux condenser, 139.5 g of compound M-1 was dissolved in 750 g of toluene. To the solution, 114.2 g of compound M-5 and 2.4 g of compound M-7 were added, and it was heated at 60° C. To the flask, 0.9 g of platinum-on-carbon catalyst (5 wt %) was admitted whereupon the internal reaction temperature rose to 65-67° C. After confirmation of this temperature rise, the flask was heated at 90° C. for 1 hour and cooled to 60° C. again. To the flask, 0.9 g of platinum-on-carbon catalyst (5 wt %) was admitted, and 50.1 g of compound M-8 was added dropwise over 1 hour. At this point, the flask internal temperature rose to 65-67° C. After the dropwise addition, the reaction solution was ripened for 3 hours at 90° C., cooled to 60° C., and ripened for 8 days. In the 8-day ripening course, each 1.8 g of platinum-on-carbon catalyst (5 wt %) was admitted on the 2nd, 3rd, 4th, 7th and 8th days. Then 700 g of methyl isobutyl ketone was added. The reaction solution was filtered through a filter under pressure to remove the platinum catalyst. To the silicone structure-bearing polymer solution thus obtained, 300 g of deionized water was added, followed by stirring and stationary holding for separation. The lower layer or water layer was removed. This washing/separatory operation was repeated 6 times, thereby removing the trace acid value from the silicone structure-bearing polymer solution. The solvent was distilled off in vacuum from the silicone structure-bearing polymer solution and instead, 700 g of cyclopentanone was added. The solution was concentrated in vacuum, yielding a silicone structure-bearing polymer solution (A-2) in cyclopentanone having a resin solids concentration of 65-70 wt %. The silicone structure-bearing polymer in the solution was measured for molecular weight by GPC versus polystyrene standards, finding a Mw of 19,000. The polymer corresponded to formula (1) wherein a=0, b=0, c=0, d=0, e=0.744, and f=0.256. W is as shown below.

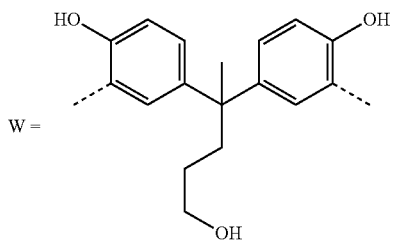

Synthesis Example 4

Synthesis of Silicone Structure-Bearing Polymer Solution (A-3)

Synthesis was carried out as in Synthesis Example 3 aside from using 51.3 g of compound M-6 instead of compound M-5, yielding a silicone structure-bearing polymer solution (A-3) in cyclopentanone. The silicone structure-bearing polymer in the solution was measured for molecular weight by GPC versus polystyrene standards, finding a Mw of 12,000. The polymer corresponded to formula (1) wherein a=0, b=0, c=0, d=0, e=0.744, and f=0.256. W is as shown below.

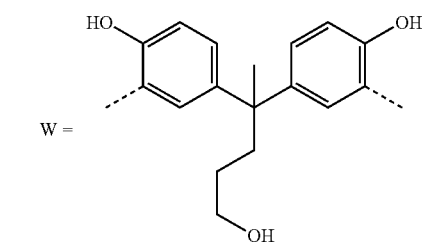

Synthesis Example 5

Synthesis of Silicone Structure-Bearing Polymer Solution (A-4)

In a 3-L flask equipped with a stirrer, thermometer, nitrogen purging line and reflux condenser, 140 g of compound M-2 was dissolved in 750 g of toluene. To the solution, 30.0 g of compound M-1, 208.7 g of compound M-4, and 2.4 g of compound M-7 were added, and it was heated at 60° C. To the flask, 0.9 g of platinum-on-carbon catalyst (5 wt %) was admitted whereupon the internal reaction temperature rose to 65-67° C. After confirmation of this temperature rise, the flask was heated at 90° C. for 1 hour and cooled to 60° C. again. To the flask, 0.9 g of platinum-on-carbon catalyst (5 wt %) was admitted, and 50.1 g of compound M-8 was added dropwise over 1 hour. At this point, the flask internal temperature rose to 65-67° C. After the dropwise addition, the reaction solution was ripened for 3 hours at 90° C., cooled to 60° C., and ripened for 8 days. In the 8-day ripening course, each 1.8 g of platinum-on-carbon catalyst (5 wt %) was admitted on the 2nd, 3rd, 4th, 7th and 8th days. Then 700 g of methyl isobutyl ketone was added. The reaction solution was filtered through a filter under pressure to remove the platinum catalyst. To the silicone structure-bearing polymer solution thus obtained, 300 g of deionized water was added, followed by stirring and stationary holding for separation. The lower layer or water layer was removed. This washing/separatory operation was repeated 6 times, thereby removing the trace acid value from the silicone structure-bearing polymer solution. The solvent was distilled off in vacuum from the silicone structure-bearing polymer solution and instead, 700 g of cyclopentanone was added. The solution was concentrated in vacuum, yielding a silicone structure-bearing polymer solution (A-4) in cyclopentanone having a resin solids concentration of 65-70 wt %. The silicone structure-bearing polymer in the solution was measured for molecular weight by GPC versus polystyrene standards, finding a Mw of 28,000. The polymer corresponded to formula (1) wherein a=0.584, b=0.201, c=0, d=0, e=0.160, and f=0.055. X and W are as shown below.

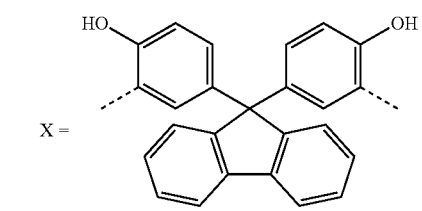

W = 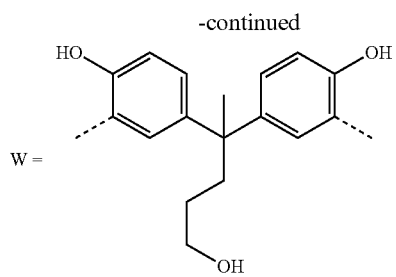

Synthesis Example 6

Synthesis of Silicone Structure-Bearing Polymer Solution (A-5)

Synthesis was carried out as in Synthesis Example 5 aside from using 100 g of compound M-2, 30.0 g of compound M-1, 236.8 g of compound M-4, 2.7 g of compound M-7, and 56.1 g of compound M-8, yielding a silicone structure-bearing polymer solution (A-5) in cyclopentanone. The silicone structure-bearing polymer in the solution was measured for molecular weight by GPC versus polystyrene standards, finding a Mw of 29,000. The polymer corresponded to formula (1) wherein a=0.385, b=0.133, c=0, d=0, e=0.358, and f=0.124. X and W are as shown below.

X = , W = 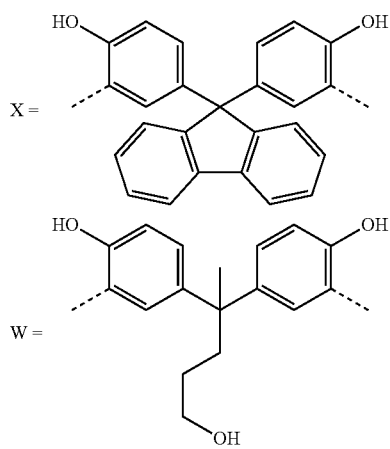

Synthesis Example 7

Synthesis of Silicone Structure-Bearing Polymer Solution (A-6)

Synthesis was carried out as in Synthesis Example 6 aside from using 68.5 g of compound M-3 instead of 100 g of compound M-2, yielding a silicone structure-bearing polymer solution (A-6) in cyclopentanone. The silicone structure-bearing polymer in the solution was measured for molecular weight by GPC versus polystyrene standards, finding a Mw of 29,000. The polymer corresponded to formula (1) wherein a=0.385, b=0.133, c=0, d=0, e=0.358, and f=0.124. X and W are as shown below.

X = , W = 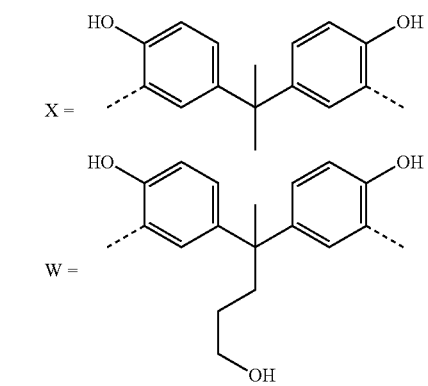

Synthesis Example 8

Synthesis of Silicone Structure-Bearing Polymer Solution (A-7)

In a 3-L flask equipped with a stirrer, thermometer, nitrogen purging line and reflux condenser, 93.5 g of compound M-9 was dissolved in 750 g of toluene. To the solution, 72.6 g of compound M-1, 236.8 g of compound M-4, and 2.6 g of compound M-7 were added, and it was heated at 60° C. To the flask, 0.9 g of platinum-on-carbon catalyst (5 wt %) was admitted whereupon the internal reaction temperature rose to 65-67° C. After confirmation of this temperature rise, the flask was heated at 90° C. for 3 hours and cooled to 60° C. again. To the flask, 0.9 g of platinum-on-carbon catalyst (5 wt %) was admitted, and 56.1 g of compound M-8 was added dropwise over 1 hour. At this point, the flask internal temperature rose to 65-67° C. After the dropwise addition, the reaction solution was ripened for 3 hours at 90° C. and cooled to room temperature. Then 700 g of methyl isobutyl ketone was added. The reaction solution was filtered through a filter under pressure to remove the platinum catalyst. To the silicone structure-bearing polymer solution thus obtained, 300 g of deionized water was added, followed by stirring and stationary holding for separation. The lower layer or water layer was removed. This washing/separatory operation was repeated 6 times, thereby removing the trace acid value from the silicone structure-bearing polymer solution. The solvent was distilled off in vacuum from the silicone structure-bearing polymer solution and instead, 700 g of cyclopentanone was added. The solution was concentrated in vacuum, yielding a silicone structure-bearing polymer solution (A-7) in cyclopentanone having a resin solids concentration of 65-70 wt %. The silicone structure-bearing polymer in the solution was measured for molecular weight by GPC versus polystyrene standards, finding a Mw of 30,000. The polymer corresponded to formula (1) wherein a=0, b=0, c=0.391, d=0.128, e=0.362, and f=0.119. Y and W are as shown below.

Y = 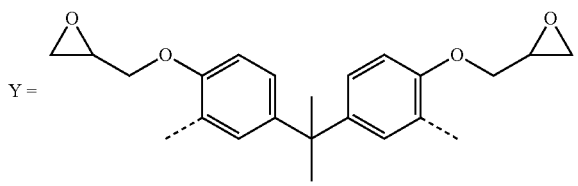

-continued

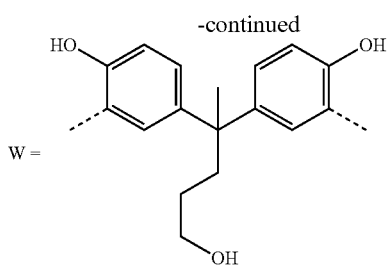

Synthesis Example 9

Synthesis of Silicone Structure-Bearing Polymer Solution (A-8)

In a 3-L flask equipped with a stirrer, thermometer, nitrogen purging line and reflux condenser, 150 g of compound M-2 and 16.6 g of compound M-9 were dissolved in 750 g of toluene. To the solution, 15.0 g of compound M-1, 211.8 g of compound M-4, and 2.3 g of compound M-7 were added, and it was heated at 60° C. To the flask, 0.9 g of platinum-on-carbon catalyst (5 wt %) was admitted whereupon the internal reaction temperature rose to 65-67° C. After confirmation of this temperature rise, the flask was heated at 90° C. for 3 hours and cooled to 60° C. again. To the flask, 0.9 g of platinum-on-carbon catalyst (5 wt %) was admitted, and 51.5 g of compound M-8 was added dropwise over 1 hour. At this point, the flask internal temperature rose to 65-67° C. After the dropwise addition, the reaction solution was ripened for 3 hours at 90° C. and cooled to room temperature. Then 700 g of methyl isobutyl ketone was added. The reaction solution was filtered through a filter under pressure to remove the platinum catalyst. To the silicone structure-bearing polymer solution thus obtained, 300 g of deionized water was added, followed by stirring and stationary holding for separation. The lower layer or water layer was removed. This washing/separatory operation was repeated 6 times, thereby removing the trace acid value from the silicone structure-bearing polymer solution. The solvent was distilled off in vacuum from the silicone structure-bearing polymer solution and instead, 700 g of cyclopentanone was added. The solution was concentrated in vacuum, yielding a silicone structure-bearing polymer solution (A-8) in cyclopentanone having a resin solids concentration of 65-70 wt %. The silicone structure-bearing polymer in the solution was measured for molecular weight by GPC versus polystyrene standards, finding a Mw of 30,000. The polymer corresponded to formula (1) wherein a=0.612, b=0.197, c=0.069, d=0.022, e=0.076, and f=0.024. X, Y and W are as shown below.

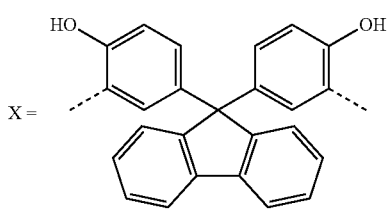

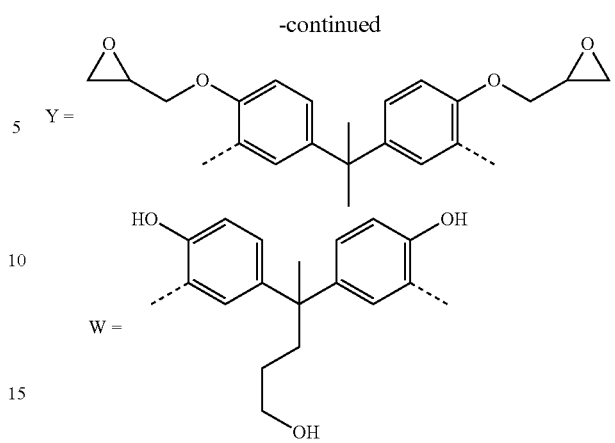

Comparative Synthesis Example 1

Synthesis of Silicone Structure-Bearing Polymer Solution (A-9)

In a 10-L flask equipped with a stirrer, thermometer, nitrogen purging line and reflux condenser, 797 g of compound M-2 was dissolved in 2,500 g of toluene. To the solution, 140.6 g of compound M-3, 1214.4 g of compound M-4, and 13.3 g of compound M-7 were added, and it was heated at 60° C. To the flask, 3.5 g of platinum-on-carbon catalyst (5 wt %) was admitted whereupon the internal reaction temperature rose to 65-67° C. After confirmation of this temperature rise, the flask was heated at 90° C. for 3 hours and cooled to 60° C. again. To the flask, 3.5 g of platinum-on-carbon catalyst (5 wt %) was admitted, and 285.2 g of compound M-8 was added dropwise over 1 hour. At this point, the flask internal temperature rose to 65-67° C. After the dropwise addition, the reaction solution was ripened for 3 hours at 90° C. and then cooled to room temperature. Then 2,800 g of methyl isobutyl ketone was added. The reaction solution was filtered through a filter under pressure to remove the platinum catalyst. To the silicone structure-bearing polymer solution thus obtained, 1,300 g of deionized water was added, followed by stirring and stationary holding for separation. The lower layer or water layer was removed. This washing/separatory operation was repeated 6 times, thereby removing the trace acid value from the silicone structure-bearing polymer solution. The solvent was distilled off in vacuum from the silicone structure-bearing polymer solution and instead, 3,300 g of cyclopentanone was added. The solution was concentrated in vacuum, yielding a silicone structure-bearing polymer solution (A-9) in cyclopentanone having a resin solids concentration of 65-70 wt %. The silicone structure-bearing polymer in the solution was measured for molecular weight by GPC versus polystyrene standards, finding a Mw of 31,000. The polymer corresponded to formula (1) wherein a=0.742, b=0.258, c=0, d=0, e=0, and f=0.

Comparative Synthesis Example 2

Synthesis of Silicone Structure-Bearing Polymer Solution (A-10)

In a 2-L flask equipped with a stirrer, thermometer, nitrogen purging line and reflux condenser, 150 g of compound M-2 was dissolved in 700 g of toluene. To the solution, 26.1 g of compound M-3, 373.4 g of compound M-4, and 2.4 g of compound M-7 were added, and it was heated at 60° C. To the flask, 0.6 g of platinum-on-carbon catalyst (5 wt %) was admitted whereupon the internal reaction temperature rose to 65-67° C. After confirmation of this temperature rise, the flask was heated at 90° C. for 3 hours and cooled to 60° C. again. To the flask, 0.7 g of platinum-on-carbon catalyst (5 wt %) was admitted, and 45.5 g of compound M-8 was added dropwise over 20 minutes. At this point, the flask internal temperature rose to 65-67° C. After the dropwise addition, the reaction solution was ripened for 3 hours at 90° C. and then cooled to room temperature. Then 670 g of methyl isobutyl ketone was added. The reaction solution was filtered through a filter under pressure to remove the platinum catalyst. To the silicone structure-bearing polymer solution thus obtained, 300 g of deionized water was added, followed by stirring and stationary holding for separation. The lower layer or water layer was removed. This washing/separatory operation was repeated 6 times, thereby removing the trace acid value from the silicone structure-bearing polymer solution. The solvent was distilled off in vacuum from the silicone structure-bearing polymer solution and instead, 780 g of cyclopentanone was added. The solution was concentrated in vacuum, yielding a silicone structure-bearing polymer solution (A-10) in cyclopentanone having a resin solids concentration of 65-70 wt %. The silicone structure-bearing polymer in the solution was measured for molecular weight by GPC versus polystyrene standards, finding a Mw of 29,000. The polymer corresponded to formula (1) wherein a=0.614, b=0.386, c=0, d=0, e=0, and f=0.

Comparative Synthesis Example 3

Synthesis of Silicone Structure-Bearing Polymer Solution (A-11)

In a 2-L flask equipped with a stirrer, thermometer, nitrogen purging line and reflux condenser, 150 g of compound M-2 was dissolved in 850 g of toluene. To the solution, 88.8 g of compound M-3, 355.2 g of compound M-4, and 3.9 g of compound M-7 were added, and it was heated at 60° C. To the flask, 0.7 g of platinum-on-carbon catalyst (5 wt %) was admitted whereupon the internal reaction temperature rose to 65-67° C. After confirmation of this temperature rise, the flask was heated at 90° C. for 3 hours and cooled to 60° C. again. To the flask, 0.7 g of platinum-on-carbon catalyst (5 wt %) was admitted, and 84.2 g of compound M-8 was added dropwise over 30 minutes. At this point, the flask internal temperature rose to 65-67° C. After the dropwise addition, the reaction solution was ripened for 3 hours at 90° C. and then cooled to room temperature. Then 770 g of methyl isobutyl ketone was added. The reaction solution was filtered through a filter under pressure to remove the platinum catalyst. To the silicone structure-bearing polymer solution thus obtained, 350 g of deionized water was added, followed by stirring and stationary holding for separation. The lower layer or water layer was removed. This washing/separatory operation was repeated 6 times, thereby removing the trace acid value from the silicone structure-bearing polymer solution. The solvent was distilled off in vacuum from the silicone structure-bearing polymer solution and instead, 930 g of cyclopentanone was added. The solution was concentrated in vacuum, yielding a silicone structure-bearing polymer solution (A-11) in cyclopentanone having a resin solids concentration of 65-70 wt %. The silicone structure-bearing polymer in the solution was measured for molecular weight by GPC versus polystyrene standards, finding a Mw of 34,000. The polymer corresponded to formula (1) wherein a=0.740, b=0.260, c=0, d=0, e=0, and f=0.

Examples and Comparative Examples

Resist compositions #1 to #8 were prepared from the polymer solutions A-1 to A-8 of Synthesis Examples 2 to 9. The polymer solution was combined with a crosslinker, PAG, an amine compound, and cyclopentanone as additional solvent in amounts as shown in Table 1, yielding a resist composition having a resin concentration of 45 wt %. The procedure involved stirring and mixing for dissolution and precision filtration through a Teflon® filter with a pore size of 0.5 μm.

In Comparative Examples, resist compositions #9 to #11 were similarly prepared by combining the polymer solutions A-9 to A-11 of Comparative Synthesis Examples 1 to 3 with a crosslinker, PAG, amine and solvent, stirring and mixing for dissolution and precision filtering through a Teflon® filter with a pore size of 0.5 μm. The formulation of Comparative Examples is also shown in Table 1.

TABLE 1

| Resist composition | Silicone structure-bearing polymer (pbw) | PAG (pbw) | Crosslinker (pbw) | Basic compound (pbw) |
|---|---|---|---|---|
| #1 | A-1 (100) | PAG-1 (1.0) | XL-1 (10.0) | Amine-1 (0.2) |
| #2 | A-2 (100) | PAG-1 (1.0) | XL-1 (10.0) | Amine-1 (0.2) |
| #3 | A-3 (100) | PAG-1 (1.0) | XL-1 (10.0) | Amine-1 (0.2) |
| #4 | A-4 (100) | PAG-1 (1.0) | XL-1 (10.0) | Amine-1 (0.2) |
| #5 | A-5 (100) | PAG-1 (1.0) | XL-1 (10.0) | Amine-1 (0.2) |
| #6 | A-6 (100) | PAG-1 (1.0) | XL-1 (10.0) | Amine-1 (0.2) |
| #7 | A-7 (100) | PAG-1 (1.0) | XL-1 (10.0) | Amine-1 (0.2) |
| #8 | A-8 (100) | PAG-1 (1.0) | XL-1 (10.0) | Amine-1 (0.2) |
| #9 | A-9 (100) | PAG-1 (1.0) | XL-1 (10.0) | Amine-1 (0.2) |
| #10 | A-10 (100) | PAG-1 (1.0) | XL-1 (10.0) | Amine-1 (0.2) |
| #11 | A-11 (100) | PAG-1 (1.0) | XL-1 (10.0) | Amine-1 (0.2) |

The acid generator PAG-1, crosslinker XL-1, and basic compound Amine-1 in Table 1 are identified below.

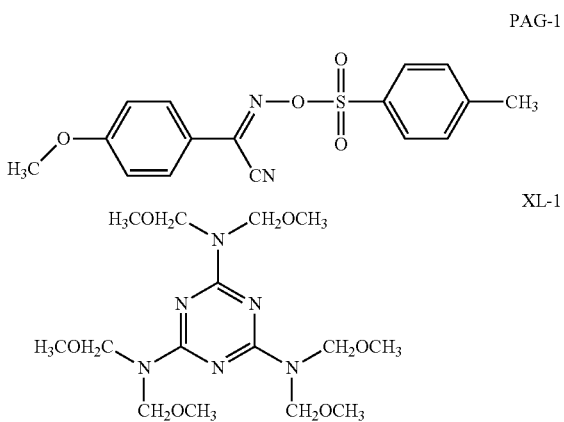

-continued

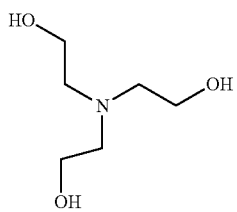

Amine-1

II. Exposure and Pattern Formation

The resist composition was coated onto a silicon substrate by spin coating. Specifically, 5 mL of the resist composition may be dispensed on the substrate, which is then spun. The buildup or thickness of the resist film on the substrate can be easily adjusted by controlling the rotational speed. The resist composition was coated onto the silicon substrate to a thickness of 20 μm.

After the resist composition was dispensed and spin coated onto the substrate, it was prebaked on a hot plate at 100° C. for 2 minutes. Next, using a mask aligner MA-8 (SUSS MicroTec AG) with a mask having a 1:1 column/row matrix of 20-μm holes, the resist film was exposed to a broad band of radiation. The substrate was baked (PEB) at 110° C. for 2 minutes and cooled. Then puddle development in isopropyl alcohol (IPA) for 1 minute was repeated 3 times for patterning the resist film. The patterned film on the substrate was post-cured in an oven at 180° C. for 2 hours while the oven was purged with nitrogen.

The resist film was similarly patterned using a SiN substrate and a Cu substrate instead of the silicon substrate.

To observe the cross-sectional profile of the resulting hole pattern, each substrate was sectioned. The profile of the hole pattern was observed under a scanning microscope (SEM). Table 2 reports the optimum dose (dose computed as 365-nm radiation) at which the hole pattern was finished to the same size (or diameter) of holes as the mask size of 20 μm.

TABLE 2

| | | Resist composition | Profile and dose (mJ/cm$^2$) on silicon | Profile and dose (mJ/cm$^2$) on SiN | Profile and dose (mJ/cm$^2$) on Cu |
|---|---|---|---|---|---|
| Example | 1 | #1 | forward taper 250 | forward taper 270 | forward taper 270 |
| | 2 | #2 | forward taper 270 | forward taper 270 | forward taper 290 |
| | 3 | #3 | forward taper 290 | forward taper 310 | forward taper 310 |
| | 4 | #4 | forward taper 250 | forward taper 270 | forward taper 270 |
| | 5 | #5 | forward taper 230 | forward taper 250 | forward taper 250 |
| | 6 | #6 | forward taper 250 | forward taper 250 | forward taper 250 |
| | 7 | #7 | forward taper 230 | forward taper 250 | forward taper 250 |
| | 8 | #8 | forward taper 250 | forward taper 270 | forward taper 270 |

TABLE 2-continued

| | | Resist composition | Profile and dose (mJ/cm$^2$) on silicon | Profile and dose (mJ/cm$^2$) on SiN | Profile and dose (mJ/cm$^2$) on Cu |
|---|---|---|---|---|---|
| Comparative Example | 1 | #9 | forward taper 230 | pattern stripped on development | pattern stripped on development |
| | 2 | #10 | forward taper 230 | pattern stripped on development | pattern stripped on development |
| | 3 | #11 | forward taper 230 | pattern stripped on development | pattern stripped on development |

As seen from Table 2, in an attempt to pattern a film of silicone structure-bearing polymer-free resist composition on the SiN and Cu substrates, the film substantially stripped off, that is, patterning was impossible. It is demonstrated that use of the silicone structure-bearing polymer in a resist composition is effective for improving the patterning of the resist composition and the adhesion between the film and the substrate.

III. Manufacture of Photo-Curable Dry Film

Photo-curable dry films were manufactured using the polymer solutions of Synthesis Examples 2, 5 to 9. Resist compositions were prepared by combining the polymer solution with a crosslinker, PAG, and amine compound in amounts as shown in Table 1 (no extra cyclopentanone as solvent). The procedure involved stirring and mixing for dissolution and precision filtration through a Teflon® filter with a pore size of 1.0 μm.

In Comparative Examples, resist compositions were similarly prepared by combining the polymer solutions of Comparative Synthesis Examples 1 to 3 with a crosslinker, PAG, and amine compound (no extra cyclopentanone as solvent), stirring and mixing for dissolution and precision filtering through a Teflon® filter with a pore size of 1.0 μm.

A die coater was used as the film coater and a polyethylene terephthalate (PET) film of 38 μm thick used as the support film. Each of resist compositions #1, #4 to #11 in Table 1 was coated onto the support film to a coating thickness of 50 μm. The coated film was passed through a hot air circulating oven (length 4 m) set at 100° C. over 5 minutes, forming a photo-curable resin layer on the support film. Using a laminating roll, a polyethylene film of 50 μm thick as the protective film was bonded to the photo-curable resin layer under a pressure of 1 MPa, yielding a photo-curable dry film.

The photo-curable resin layer had a thickness of 50 μm. Dry films in Examples and Comparative Examples are shown in Table 3.

IV. Exposure and Pattern Formation

From each of the photo-curable dry films using the resist compositions in Examples and Comparative Examples as tabulated in Table 3, the protective film was stripped off. Using a vacuum laminator TEAM-100RF (Takatori Corp.) with a vacuum chamber set at a vacuum of 100 Pa and a temperature of 100° C., the photo-curable resin layer on the support film was closely bonded to a silicon substrate. After restoration of atmospheric pressure, the substrate was cooled to 25° C. and taken out of the laminator. The support film was stripped off.

After the support film was stripped off, the photo-curable resin layer on substrate was prebaked on a hot plate at 100° C. for 5 minutes. Next, using a mask aligner MA-8 (SUSS MicroTec AG) with a mask having a 1:1 column/row matrix of 40-μm holes, the resin layer was exposed to a broad band of radiation. The substrate was baked (PEB) at 130° C. for 5 minutes and cooled. This was followed by spray development in propylene glycol monomethyl ether acetate (PGMEA) for 5 minutes for patterning the resin layer. The patterned layer on the substrate was post-cured in an oven at 180° C. for 2 hours while the oven was purged with nitrogen.

The photo-curable dry film was similarly laminated and patterned using a SiN substrate and a Cu substrate instead of the silicon substrate.

To observe the cross-sectional profile of the resulting hole pattern, each substrate was sectioned. The profile of the hole pattern was observed under SEM. Table 3 reports the optimum dose (dose computed as 365-nm radiation) at which the hole pattern was finished to the same size (or diameter) of holes as the mask size of 40 μm.

TABLE 3

| | | Resist composition | Profile and dose (mJ/cm$^2$) on silicon | Profile and dose (mJ/cm$^2$) on SiN | Profile and dose (mJ/cm$^2$) on Cu |
|---|---|---|---|---|---|
| Example | 9 | #1 | forward taper 300 | forward taper 320 | forward taper 320 |
| | 10 | #4 | forward taper 300 | forward taper 320 | forward taper 320 |
| | 11 | #5 | forward taper 280 | forward taper 300 | forward taper 300 |
| | 12 | #6 | forward taper 300 | forward taper 300 | forward taper 300 |
| | 13 | #7 | forward taper 280 | forward taper 300 | forward taper 300 |
| | 14 | #8 | forward taper 300 | forward taper 300 | forward taper 320 |
| Comparative Example | 4 | #9 | forward taper 280 | pattern stripped on development | pattern stripped on development |
| | 5 | #10 | forward taper 280 | pattern stripped on development | pattern stripped on development |
| | 6 | #11 | forward taper 280 | pattern stripped on development | pattern stripped on development |

As seen from Table 3, in an attempt to laminate and pattern a photo-curable dry film comprising a silicone structure-bearing polymer-free composition on the SiN and Cu substrates, the film substantially stripped off, that is, patterning was impossible. It is demonstrated that the use of the silicone structure-bearing polymer in a resist composition is effective for improving the patterning of the photo-curable dry film and the adhesion between the pattern (or film) and the substrate.

V. Filling Capability

There were provided 6-inch silicon wafers which each were perforated with 200 circular holes having an opening diameter of 10 to 100 μm (increment 10 μm) and a depth of 10 to 120 μm (increment 10 μm). The photo-curable dry films of Examples 15 to 17 in Table 4 were tested. The protective film was stripped off from each of the photo-curable dry films. Using a vacuum laminator TEAM-100RF (Takatori Corp.) with a vacuum chamber set at a vacuum of 100 Pa and a temperature of 100° C., the photo-curable resin layer on the support film was closely bonded to the silicon substrate. After restoration of atmospheric pressure, the substrate was cooled to 25° C. and taken out of the laminator. The support film was stripped off.

After the support film was stripped off, the photo-curable resin layer on substrate was prebaked on a hot plate at 100° C. for 5 minutes. Next, using a mask aligner MA-8 (SUSS MicroTec AG), the resin layer was exposed to a broad band of radiation in a dose (wavelength 365 nm) as shown in Table 4. The substrate was baked (PEB) at 110° C. for 5 minutes and cooled. This was followed by spray development in PGMEA for 5 minutes for patterning the resin layer. The patterned layer on the substrate was post-cured in an oven at 180° C. for 2 hours while the oven was purged with nitrogen.

The substrate was diced so that the circular holes might be viewed in cross section. The cross section of the circular holes was observed under SEM to inspect whether or not voids were left. The results are reported in Table 4.

TABLE 4

| Film | | Resist composition | Dose (mJ/cm$^2$) | Cross section of circular holes observed |
|---|---|---|---|---|
| Example | 15 | #1 | 350 | no voids, fully filled |
| | 16 | #4 | 350 | no voids, fully filled |
| | 17 | #5 | 350 | no voids, fully filled |

As seen from Table 4, the holes were fully filled without leaving voids. It is demonstrated that the photo-curable dry film, specifically photo-curable resin layer exhibits satisfactory filling or embedment as the electric/electronic part-protecting film.

VI. Electric Properties (Dielectric Breakdown Strength)

The photo-curable dry films of Examples 15 to 17 (resin layer thickness 50 μm) in Table 4 were tested. After the protective film was stripped off, the photo-curable resin layer on the support film was closely bonded to a substrate (according to JIS K-6249) at a temperature of 100° C. The assembly was cooled to room temperature, after which the support film was stripped off. The photo-curable resin layer on substrate was prebaked on a hot plate at 100° C. for 5 minutes. Next, using the mask aligner, the resin layer was exposed to a broad band of radiation in a dose of 1,000 mJ/cm$^2$ (wavelength 365 nm) through a quartz photomask. The substrate was baked (PEB) at 110° C. for 5 minutes and cooled. This was followed by spray development in PGMEA for 5 minutes. The layer on the substrate was post-cured in an oven at 180° C. for 2 hours while the oven was purged with nitrogen. The substrate having the cured layer thereon was measured for dielectric breakdown strength according to JIS K-6249, with the results shown in Table 5.

As seen from Table 5, all the layers had satisfactory electric property as the electric/electronic part-protecting film.

VII. Adhesion

The photo-curable dry films of Examples 15 to 17 (resin layer thickness 50 μm) in Table 4 were tested. The protective film was stripped off. Using the vacuum laminator, the photo-curable resin layer on the support film was closely bonded to a neat 6-inch silicon wafer in a vacuum chamber set at a vacuum of 100 Pa and a temperature of 100° C. After restoration of atmospheric pressure, the substrate was cooled to 25° C. and taken out of the laminator. The support film was stripped off. Thereafter, the photo-curable resin layer on substrate was prebaked on a hot plate at 100° C. for 5 minutes. Next, using the mask aligner, the resin layer was exposed to a broad band of radiation in a dose of 1,000 mJ/cm$^2$ (wavelength 365 nm) through a quartz photomask. The substrate was baked (PEB) at 110° C. for 5 minutes and cooled. This was followed by spray development in PGMEA for 5 minutes. The layer on the substrate was post-cured in an oven at 180° C. for 2 hours while the oven was purged with nitrogen, yielding a patterned post-cured film having pattern features with a diameter of 300 μm and a height of 50 μm. The patterned post-cured film was evaluated for initial adhesion by peeling the film from the substrate and measuring the reaction force. The measurement conditions included a bond tester (page series 4000-PXY by Dage), a speed of 50.0 μm/sec, and a height of 3.0 μm.

FIG. 1 schematically illustrates how to evaluate adhesion or bond strength. A patterned post-cured film 2 is borne on a silicon substrate 1. A jig 3 of the bond tester is moved in the direction of arrow 4 to push the film. Measurements at 15 points were averaged. A higher value indicates greater adhesion of the patterned post-cured film to the substrate.

Further, a solder flux fluid was applied to the patterned post-cured film on the substrate. The film was heated at 220° C. for 30 seconds, cooled, washed with deionized water, and dried at room temperature for 2 hours. After this degradation test, the patterned post-cured film was evaluated for adhesion again by using the bond tester, peeling the film from the substrate and measuring the reaction force.

For the three photo-curable dry films, adhesion was evaluated by comparing their initial values. Chemical resistance (against solder flux) was also evaluated by comparing their adhesion behavior that the bond strength decreases from the initial value to the post-degradation value. The results are shown in Table 5.

As seen from Table 5, the layers had satisfactory adhesion as the electric/electronic part-protecting film.

VIII. Crack Resistance

The photo-curable dry films of Examples 15 to 17 (resin layer thickness 50 μm) in Table 4 were tested. The protective film was stripped off. Using the vacuum laminator, the photo-curable resin layer on the support film was closely bonded to a substrate (used in the filling test) in a vacuum chamber at a vacuum of 100 Pa and a temperature of 100° C. After restoration of atmospheric pressure, the substrate was cooled to 25° C. and taken out of the laminator. The support film was stripped off.

Thereafter, the photo-curable resin layer on substrate was prebaked on a hot plate at 100° C. for 5 minutes. Next, using the mask aligner, the resin layer was exposed to a broad band of radiation in a dose of 1,000 mJ/cm² (wavelength 365 nm) through a quartz photomask. The substrate was baked (PEB) at 110° C. for 5 minutes and cooled. This was followed by spray development in PGMEA for 5 minutes. The layer on the substrate was post-cured in an oven at 180° C. for 2 hours while the oven was purged with nitrogen.

The substrate having the cured film thereon was placed in a thermal cycling tester where thermal cycling between −55° C. and +150° C. was repeated until 1,000 cycles. During the test, the cured film was observed whether or not cracks formed. The results are shown in Table 5.

As seen from Table 5, the layers had satisfactory crack resistance as the electric/electronic part-protecting film.

IX. Resistance to Stripper

The photo-curable dry films of Examples 15 to 17 (resin layer thickness 50 μm) in Table 4 were tested. The protective film was stripped off. Using the vacuum laminator, the photo-curable resin layer on the support film was closely bonded to a neat 6-inch silicon wafer in a vacuum chamber at a vacuum of 100 Pa and a temperature of 100° C. After restoration of atmospheric pressure, the substrate was cooled to 25° C. and taken out of the laminator. The support film was stripped off.

Thereafter, the photo-curable resin layer on substrate was prebaked on a hot plate at 100° C. for 5 minutes. Next, using the mask aligner, the resin layer was exposed to a broad band of radiation in a dose of 1,000 mJ/cm² (wavelength 365 nm) through a quartz photomask. The substrate was baked (PEB) at 110° C. for 5 minutes and cooled. This was followed by spray development in PGMEA for 5 minutes. The layer on the substrate was post-cured in an oven at 180° C. for 2 hours while the oven was purged with nitrogen, yielding a cured film having a pattern of 15 mm×15 mm squares. The film was immersed in N-methylpyrrolidone (NMP) at room temperature for 1 hour. By examining film thickness change and outer appearance, the film was evaluated for stripper resistance. The results are also shown in Table 5.

As seen from Table 5, all the layers had satisfactory stripper resistance as the electric/electronic part-protecting film.

TABLE 5

| Film | Dielectric breakdown strength (V/μm) | Adhesion (mN) | | Crack resistance after thermal cycling | Stripper resistance after immersion in NMP |
|---|---|---|---|---|---|
| | | Initial | Degraded | | |
| Example 15 | 350 | 340 | 270 | no cracks | appearance and thickness unchanged |
| 16 | 350 | 330 | 270 | no cracks | appearance and thickness unchanged |
| 17 | 350 | 370 | 270 | no cracks | appearance and thickness unchanged |

Japanese Patent Application No. 2014-153677 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A silicone structure-bearing polymer comprising recurring units of the general formula (1) and having a weight average molecular weight of 3,000 to 500,000,

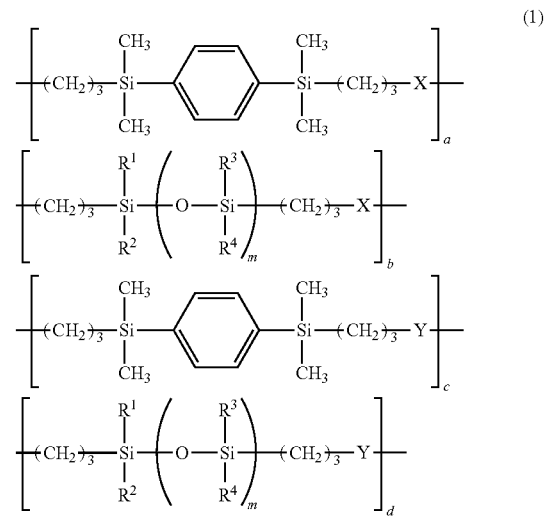

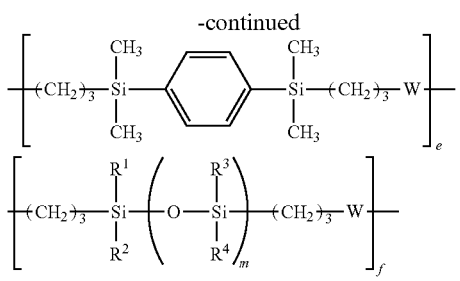

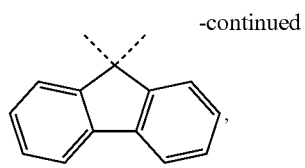

wherein $R^1$ to $R^4$ are each independently a monovalent $C_1$-$C_8$ hydrocarbon group, m is an integer of 1 to 100, a, b, c and d are each independently 0 or a positive number, e and f each are a positive number, and a+b+c+d+e+f=1, X is an organic group having the general formula (2):

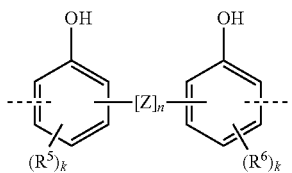
(2)

wherein Z is a divalent organic group selected from the group consisting of

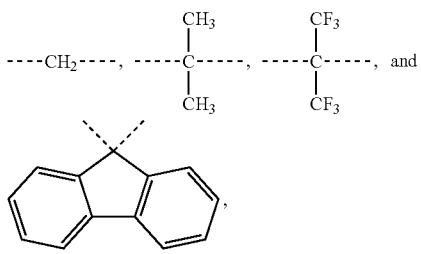

the broken line segment denotes a valence bond, n is 0 or 1, $R^5$ and $R^6$ are each independently a $C_1$-$C_4$ alkyl or alkoxy group, k is 0, 1 or 2, Y is an organic group having the general formula (3):

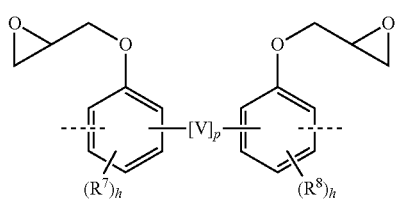
(3)

wherein V is a divalent organic group selected from the group consisting of

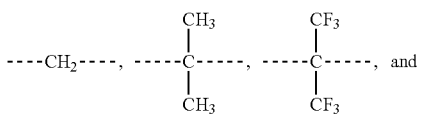

the broken line segment denotes a valence bond, p is 0 or 1, $R^7$ and $R^8$ are each independently a $C_1$-$C_4$ alkyl or alkoxy group, h is 0, 1 or 2, and W is an organic group having the general formula (4):

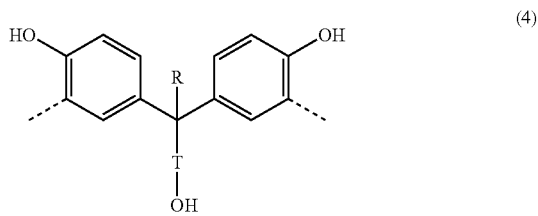
(4)

wherein the broken line segment denotes a valence bond, R is hydrogen or a straight or branched $C_1$-$C_6$ alkyl group, and T is a straight, branched or cyclic $C_1$-$C_{12}$ alkylene group.

2. The polymer of claim 1 wherein W is an organic group having the general formula (5):

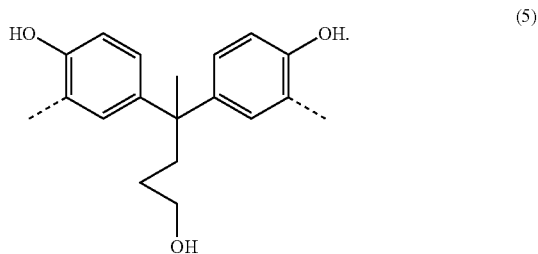
(5)

3. The polymer of claim 1 wherein in formula (1), $0.1 \leq a \leq 0.8$, $0.1 \leq b \leq 0.8$, $0 \leq c$, $0 \leq d$, $0 < e \leq 0.8$, and $0 < f \leq 0.8$.

4. A chemically amplified negative resist composition comprising
(A) the silicone structure-bearing polymer having a weight average molecular weight of 3,000 to 500,000, of claim 1,
(B) a photoacid generator which is decomposed to generate an acid upon exposure to radiation of wavelength 190 to 500 nm,
(C) at least one crosslinker selected from the group consisting of an amino condensate modified with formaldehyde or formaldehyde-alcohol, a phenol compound having on the average at least two methylol or alkoxymethylol groups in the molecule, a polyhydric phenol compound in which at least one hydrogen atom of hydroxyl group is substituted by a glycidyl group, a polyhydric phenol compound in which at least one hydrogen atom of hydroxyl group is substituted by a group of the formula (C-1), and a compound containing at least two structures each having nitrogen bonded to a glycidyl group, the structure having the formula (C-2) or (C-3),

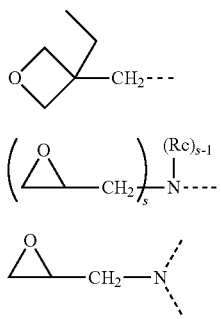

wherein the broken line segment denotes a valence bond, Rc is a straight, branched or cyclic $C_1$-$C_6$ alkyl group, and s is 1 or 2, and (D) a solvent.

5. A pattern forming process comprising the steps of:
(1) coating the chemically amplified negative resist composition of claim 4 onto a substrate, and prebaking to form a resist film,
(2) exposing the resist film to high-energy radiation of wavelength 190 to 500 nm or electron beam through a photomask,
(3) baking and developing in a developer to pattern the resist film.

6. The process of claim 5, further comprising (4) post-curing the patterned resist film resulting from development step (3) at a temperature of 100 to 250° C.

7. An electric/electronic part protective film comprising the post-cured patterned resist film obtained by the process of claim 6.

8. A photo-curable dry film comprising a photo-curable resin layer having a thickness of 10 to 100 μm sandwiched between a support film and a protective film, the photo-curable resin layer being formed of the chemically amplified negative resist composition of claim 4.

9. A method for preparing a photo-curable dry film, comprising the steps of:
(i) continuously coating the chemically amplified negative resist composition of claim 4 onto a support film,
(ii) continuously drying the composition to form a photo-curable resin layer on the support film, and
(iii) applying a protective film onto the photo-curable resin layer.

10. A pattern forming process comprising the steps of:
(i) stripping the protective film from the photo-curable dry film of claim 8 and placing the bare photo-curable resin layer in close contact with a substrate,
(ii) exposing the photo-curable resin layer to high-energy radiation of wavelength 190 to 500 nm or EB through a photomask and through the support film or with the support film stripped off,
(iii) post-exposure bake, and
(iv) developing in a developer to pattern the layer.

11. The process of claim 10, further comprising (v) post-curing the patterned layer resulting from development step (iv) at a temperature of 100 to 250° C.

12. The process of claim 10 wherein the substrate is provided with grooves and/or holes having an opening width of 10 to 100 μm and a depth of 10 to 120 μm.

13. A laminate comprising
a substrate provided with grooves and/or holes having an opening width of 10 to 100 μm and a depth of 10 to 120 μm, and
a layer lying on the substrate, the layer being a photo-curable resin layer formed of the chemically amplified negative resist composition of claim 10.

14. A bis(4-hydroxy-3-allylphenyl) derivative having an alcoholic hydroxyl group, represented by the general formula (6):

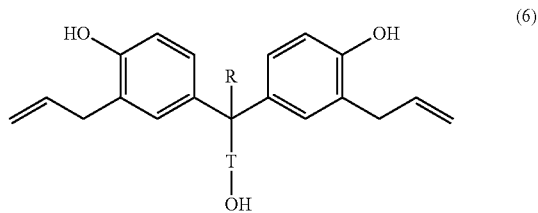

wherein R is hydrogen or a straight or branched $C_1$-$C_6$ alkyl group and T is a straight, branched or cyclic $C_1$-$C_{12}$ alkylene group.

15. 4,4-bis(4-hydroxy-3-allylphenyl)pentanol represented by the formula (7):

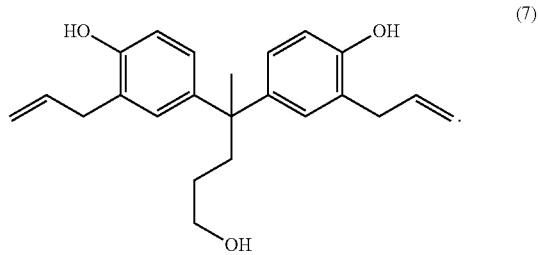 [SMILES: C=CCc1cc(C(C)(CCCO)c2ccc(O)c(CC=C)c2)ccc1O]

* * * * *